(12) United States Patent
Lamont

(10) Patent No.: US 9,447,469 B2
(45) Date of Patent: Sep. 20, 2016

(54) IDENTIFICATION OF GENETIC VARIANTS

(71) Applicant: RANDOX LABORATORIES LTD., Crumlin (GB)

(72) Inventor: John V. Lamont, Crumlin (GB)

(73) Assignee: RANDOX LABORATORIES LTD. (GB)

( * ) Notice: Subject to any disclaimer, the term of this patent is extended or adjusted under 35 U.S.C. 154(b) by 0 days.

(21) Appl. No.: 14/323,775

(22) Filed: Jul. 3, 2014

(65) Prior Publication Data

US 2015/0098937 A1    Apr. 9, 2015

Related U.S. Application Data

(62) Division of application No. 13/594,721, filed on Aug. 24, 2012, now abandoned.

(60) Provisional application No. 61/527,531, filed on Aug. 25, 2011.

(51) Int. Cl.
| | |
|---|---|
| *C12Q 1/68* | (2006.01) |
| *C12P 19/34* | (2006.01) |
| *A61K 31/404* | (2006.01) |
| *A61K 31/4439* | (2006.01) |
| *A61K 31/517* | (2006.01) |

(52) U.S. Cl.
CPC ........... *C12Q 1/6883* (2013.01); *A61K 31/404* (2013.01); *A61K 31/4439* (2013.01); *A61K 31/517* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 6,582,908 B2 | 6/2003 | Fodor et al. | |
| 2006/0073506 A1 | 4/2006 | Christians et al. | |

OTHER PUBLICATIONS ss172911331, for rs6921438; dbSNP, NCBI, NLM, 2009.*
Loomis et al; Annals of Oncology, vol. 21, p. vi26, 2010.*
ss172911331 (dbSNP, NCBI, NLM 2009).

* cited by examiner

*Primary Examiner* — Jehanne Sitton
(74) *Attorney, Agent, or Firm* — Saliwanchik, Lloyd & Eisenschenk

(57) ABSTRACT

The present disclosure provides a method for identifying whether a subject is more or less likely to be responsive to VEGF-based therapy, comprising screening a nucleic acid sample obtained from the subject to provide output information which identifies the presence or absence of an allelic variant, wherein the presence or absence of an allelic variant indicates whether the subject is more or less likely to be responsive to VEGF-based therapy.

21 Claims, 12 Drawing Sheets

| SNP | Chr | Position | CA | CAF | beta | SE | P | Gene 1 | Distance | Gene 2 | Distance | Function | O/E ratio | Imputed |
|---|---|---|---|---|---|---|---|---|---|---|---|---|---|---|
| rs6921438 | 6 | 44033585 | G | 0.52 | 0.72 | 0.01 | 6.11E-506 | MGC45491 | 42731 | MRPL14 | 155764 | INTERGENIC | 0.99 | 0 |
| rs7767396 | 6 | 44035028 | G | 0.47 | -0.71 | 0.02 | 1.71E-482 | MGC45491 | 41286 | MRPL14 | 154321 | INTERGENIC | 0.99 | 1 |
| rs4513773 | 6 | 44033504 | G | 0.46 | -0.71 | 0.02 | 2.08E-482 | MGC45491 | 42812 | MRPL14 | 155845 | INTERGENIC | 1.00 | 0 |
| rs9472159 | 6 | 44027673 | C | 0.51 | 0.76 | 0.02 | 4.30E-452 | MGC45491 | 48643 | MRPL14 | 161676 | INTERGENIC | 0.52 | 1 |
| rs9369434 | 6 | 44026385 | C | 0.53 | 0.85 | 0.02 | 2.15E-442 | MGC45491 | 49931 | MRPL14 | 162964 | INTERGENIC | 0.66 | 1 |
| rs6916314 | 6 | 44027140 | G | 0.38 | 0.92 | 0.02 | 3.13E-400 | MGC45491 | 49176 | MRPL14 | 162209 | INTERGENIC | 0.54 | 1 |
| rs9472158 | 6 | 44026875 | G | 0.38 | 0.92 | 0.02 | 6.22E-400 | MGC45491 | 49441 | MRPL14 | 162474 | INTERGENIC | 0.54 | 1 |
| rs6916540 | 6 | 44027394 | C | 0.40 | 0.87 | 0.02 | 3.60E-364 | MGC45491 | 48922 | MRPL14 | 161955 | INTERGENIC | 0.56 | 1 |
| rs9472173 | 6 | 44041234 | C | 0.47 | 0.93 | 0.02 | 1.16E-355 | MGC45491 | 35082 | MRPL14 | 148115 | INTERGENIC | 0.47 | 1 |
| rs729391 | 6 | 44025870 | C | 0.39 | 1.05 | 0.03 | 7.17E-355 | MGC45491 | 50446 | MRPL14 | 163479 | INTERGENIC | 0.38 | 1 |
| rs7764227 | 6 | 44021966 | G | 0.26 | 1.32 | 0.04 | 1.41E-228 | MGC45491 | 54350 | VEGFA | 159767 | INTERGENIC | 0.22 | 1 |
| rs9369433 | 6 | 44022528 | C | 0.23 | 1.28 | 0.04 | 6.87E-225 | MGC45491 | 53788 | VEGFA | 160329 | INTERGENIC | 0.25 | 1 |
| rs1359617 | 6 | 44024870 | T | 0.11 | 1.87 | 0.06 | 1.56E-194 | MGC45491 | 51446 | VEGFA | 162671 | INTERGENIC | 0.18 | 1 |
| rs865585 | 6 | 44019529 | C | 0.29 | 0.83 | 0.04 | 3.16E-125 | MGC45491 | 56787 | VEGFA | 157330 | INTERGENIC | 0.30 | 1 |
| rs6458360 | 6 | 44028870 | T | 0.11 | 1.10 | 0.05 | 3.14E-89 | MGC45491 | 47446 | MRPL14 | 160479 | INTERGENIC | 0.28 | 1 |
| rs17209449 | 6 | 44043245 | C | 0.09 | -1.20 | 0.06 | 1.30E-76 | MGC45491 | 33071 | MRPL14 | 146104 | INTERGENIC | 0.24 | 1 |
| rs10738760 | 9 | 2681186 | A | 0.49 | 0.28 | 0.02 | 1.96E-34 | KCNV2 | 26339 | VLDLR | 36701 | INTERGENIC | 0.68 | 1 |
| rs10757631 | 9 | 2680295 | G | 0.47 | -0.26 | 0.02 | 2.30E-32 | KCNV2 | 27230 | VLDLR | 35810 | INTERGENIC | 0.73 | 1 |
| rs6479919 | 9 | 2662809 | T | 0.37 | -0.24 | 0.02 | 3.63E-32 | VLDLR | 18324 | KCNV2 | 44716 | INTERGENIC | 0.95 | 1 |
| rs6479920 | 9 | 2663933 | A | 0.37 | -0.24 | 0.02 | 3.76E-32 | VLDLR | 19448 | KCNV2 | 43592 | INTERGENIC | 0.96 | 1 |
| rs10120651 | 9 | 2666360 | G | 0.37 | -0.23 | 0.02 | 8.60E-32 | VLDLR | 21875 | KCNV2 | 41165 | INTERGENIC | 1.01 | 1 |
| rs10120652 | 9 | 2667012 | T | 0.37 | -0.23 | 0.02 | 8.69E-32 | VLDLR | 22527 | KCNV2 | 40513 | INTERGENIC | 1.01 | 0 |
| rs10738758 | 9 | 2672355 | G | 0.37 | -0.23 | 0.02 | 9.11E-32 | VLDLR | 27870 | KCNV2 | 35170 | INTERGENIC | 0.98 | 1 |
| rs4741756 | 9 | 2658187 | C | 0.28 | -0.25 | 0.02 | 2.95E-31 | VLDLR | 13702 | KCNV2 | 49338 | INTERGENIC | 0.97 | 0 |
| rs2375980 | 9 | 2682622 | G | 0.42 | -0.25 | 0.02 | 1.30E-27 | VLDLR | 24903 | KCNV2 | 38137 | INTERGENIC | 0.70 | 1 |
| rs7856084 | 9 | 2672943 | C | 0.39 | -0.22 | 0.02 | 1.75E-27 | VLDLR | 28458 | KCNV2 | 34582 | INTERGENIC | 0.97 | 1 |
| rs10125071 | 9 | 2669579 | C | 0.40 | -0.21 | 0.02 | 5.88E-27 | VLDLR | 25094 | KCNV2 | 37946 | INTERGENIC | 1.00 | 1 |
| rs4317630 | 9 | 2671025 | C | 0.39 | -0.21 | 0.02 | 9.65E-27 | VLDLR | 26540 | KCNV2 | 36500 | INTERGENIC | 0.98 | 1 |
| rs10122587 | 9 | 2681951 | T | 0.28 | -0.22 | 0.02 | 3.02E-24 | KCNV2 | 25574 | VLDLR | 37466 | INTERGENIC | 0.97 | 1 |
| rs9361273 | 6 | 44084246 | G | 0.01 | 5.92 | 0.59 | 5.37E-24 | MGC45491 | 3381 | MRPL14 | 105103 | DOWNSTREAM | 0.03 | 1 |
| rs7747448 | 6 | 43990902 | A | 0.34 | -0.25 | 0.03 | 6.88E-23 | MGC45491 | 85414 | VEGFA | 128703 | INTRONIC | 0.58 | 1 |

FIG. 6A

| SNP | Chr | Position | CA | CAF | beta | SE | P | Gene 1 | Distance | Gene 2 | Distance | Function | O/E ratio | Imputed |
|---|---|---|---|---|---|---|---|---|---|---|---|---|---|---|
| rs4276495 | 6 | 43991237 | T | 0.32 | -0.23 | 0.02 | 6.46E-22 | MGC45491 | 85079 | VEGFA | 129038 | INTRONIC | 0.69 | 1 |
| rs10117473 | 9 | 2670425 | G | 0.21 | -0.22 | 0.02 | 7.67E-22 | VLDLR | 25940 | KCNV2 | 37100 | INTERGENIC | 1.01 | 1 |
| rs10967492 | 9 | 2671175 | A | 0.21 | -0.22 | 0.02 | 1.02E-21 | VLDLR | 26690 | KCNV2 | 36350 | INTERGENIC | 1.01 | 1 |
| rs10967470 | 9 | 2665898 | G | 0.24 | -0.22 | 0.02 | 1.17E-21 | VLDLR | 21213 | KCNV2 | 41827 | INTERGENIC | 0.97 | 1 |
| rs10812475 | 9 | 2681546 | C | 0.21 | -0.22 | 0.02 | 1.84E-21 | KCNV2 | 25979 | VLDLR | 37061 | INTERGENIC | 0.98 | 1 |
| rs10812474 | 9 | 2681446 | G | 0.21 | -0.22 | 0.02 | 1.86E-21 | KCNV2 | 26079 | VLDLR | 36961 | INTERGENIC | 0.98 | 1 |
| rs10812473 | 9 | 2681329 | A | 0.21 | -0.22 | 0.02 | 1.86E-21 | KCNV2 | 26196 | VLDLR | 36844 | INTERGENIC | 0.98 | 1 |
| rs10812471 | 9 | 2680980 | T | 0.21 | -0.22 | 0.02 | 1.89E-21 | KCNV2 | 26545 | VLDLR | 36495 | INTERGENIC | 0.99 | 1 |
| rs10125245 | 9 | 2678244 | T | 0.21 | -0.22 | 0.02 | 2.09E-21 | KCNV2 | 28281 | VLDLR | 34759 | INTERGENIC | 1.00 | 1 |
| rs10967512 | 9 | 2673939 | C | 0.21 | -0.22 | 0.02 | 2.18E-21 | VLDLR | 29454 | KCNV2 | 33586 | INTERGENIC | 1.02 | 0 |
| rs10757628 | 9 | 2674656 | T | 0.21 | -0.22 | 0.02 | 2.22E-21 | VLDLR | 30171 | KCNV2 | 32869 | INTERGENIC | 1.01 | 0 |
| rs10812472 | 9 | 2681095 | G | 0.20 | -0.23 | 0.02 | 4.89E-21 | KCNV2 | 26430 | VLDLR | 36610 | INTERGENIC | 0.94 | 0 |
| rs7867894 | 9 | 2665867 | C | 0.25 | -0.21 | 0.02 | 8.62E-21 | VLDLR | 21382 | KCNV2 | 41658 | INTERGENIC | 0.98 | 1 |
| rs9472175 | 6 | 44042760 | T | 0.15 | -0.56 | 0.06 | 9.73E-21 | MGC45491 | 33556 | MRPL14 | 146589 | INTERGENIC | 0.20 | 1 |
| rs1776717 | 6 | 44059314 | A | 0.21 | -0.23 | 0.02 | 8.10E-20 | MGC45491 | 17002 | MRPL14 | 130035 | INTERGENIC | 0.86 | 1 |
| rs910609 | 6 | 44059634 | A | 0.21 | -0.23 | 0.02 | 9.14E-20 | MGC45491 | 16682 | MRPL14 | 129715 | INTERGENIC | 0.86 | 1 |
| rs833623 | 6 | 44065755 | C | 0.41 | 0.18 | 0.02 | 1.07E-19 | MGC45491 | 69561 | VEGFA | 144556 | INTRONIC | 0.92 | 1 |
| rs833622 | 6 | 44068382 | T | 0.40 | 0.17 | 0.02 | 1.21E-19 | MGC45491 | 67934 | VEGFA | 146183 | INTRONIC | 0.98 | 0 |
| rs17767721 | 6 | 43998961 | T | 0.30 | -0.18 | 0.02 | 1.52E-19 | MGC45491 | 77355 | VEGFA | 136762 | INTRONIC | 0.89 | 0 |
| rs9361267 | 6 | 44013484 | G | 0.41 | 0.17 | 0.02 | 3.15E-19 | MGC45491 | 62832 | VEGFA | 151285 | 3PRIME UTR | 0.97 | 0 |
| rs1868979 | 6 | 44012879 | G | 0.41 | 0.17 | 0.02 | 3.72E-19 | MGC45491 | 63437 | VEGFA | 150660 | 3PRIME UTR | 0.97 | 0 |
| rs10122524 | 9 | 2681667 | T | 0.30 | -0.19 | 0.02 | 3.73E-19 | KCNV2 | 25858 | VLDLR | 37182 | INTERGENIC | 0.99 | 1 |
| rs9472155 | 6 | 44005705 | A | 0.22 | -0.20 | 0.02 | 4.45E-19 | MGC45491 | 70611 | VEGFA | 143506 | INTRONIC | 0.98 | 1 |
| rs7767550 | 6 | 44007230 | A | 0.22 | -0.20 | 0.02 | 6.36E-19 | MGC45491 | 69086 | VEGFA | 145031 | INTRONIC | 0.99 | 0 |
| rs3888006 | 6 | 44000916 | A | 0.22 | -0.20 | 0.02 | 7.60E-19 | MGC45491 | 75400 | VEGFA | 138717 | INTRONIC | 0.95 | 1 |
| rs17505670 | 6 | 44000213 | T | 0.22 | -0.20 | 0.02 | 8.79E-19 | MGC45491 | 76103 | VEGFA | 138014 | INTRONIC | 0.95 | 1 |
| rs1326141 | 6 | 44011255 | A | 0.22 | -0.20 | 0.02 | 2.43E-18 | MGC45491 | 65061 | VEGFA | 149056 | INTRONIC | 0.98 | 0 |
| rs910608 | 6 | 44059804 | C | 0.22 | -0.21 | 0.02 | 3.39E-18 | MGC45491 | 16512 | MRPL14 | 129545 | INTERGENIC | 0.87 | 1 |
| rs7356919 | 9 | 43993343 | A | 0.22 | -0.20 | 0.02 | 5.37E-18 | MGC45491 | 76973 | VEGFA | 137144 | INTRONIC | 0.96 | 1 |
| rs910610 | 6 | 44059418 | A | 0.23 | -0.21 | 0.03 | 2.50E-17 | MGC45491 | 16898 | MRPL14 | 129931 | INTERGENIC | 0.79 | 1 |
| rs1418898 | 6 | 44027285 | A | 0.01 | -2.60 | 0.31 | 7.27E-17 | MGC45491 | 49031 | MRPL14 | 162064 | INTERGENIC | 0.14 | 0 |
| rs1418897 | 6 | 44027365 | G | 0.01 | -2.60 | 0.31 | 7.37E-17 | MGC45491 | 48951 | MRPL14 | 161984 | INTERGENIC | 0.14 | 1 |
| rs9296424 | 6 | 44043864 | C | 0.18 | -0.49 | 0.06 | 9.98E-17 | MGC45491 | 32452 | MRPL14 | 145485 | INTERGENIC | 0.18 | 1 |

FIG. 6B

| SNP | Chr | Position | CA | CAF | beta | SE | P | Gene 1 | Distance | Gene 2 | Distance | Function | O:E ratio | Imputed |
|---|---|---|---|---|---|---|---|---|---|---|---|---|---|---|
| rs16831938 | 6 | 44060024 | A | 0.23 | -0.20 | 0.02 | 1.74E-16 | MGC45491 | 16292 | MRPL14 | 129325 | INTERGENIC | 0.83 | 1 |
| rs7761865 | 6 | 43976194 | G | 0.36 | -0.61 | 0.06 | 2.21E-16 | MGC45491 | 100122 | VEGFA | 113995 | INTRONIC | 0.10 | 1 |
| rs6993770 | 8 | 106650704 | T | 0.32 | -0.17 | 0.02 | 2.50E-16 | ZFPM2 | 0 | LRP12 | 980360 | INTRONIC | 0.97 | 1 |
| rs9367181 | 6 | 44064593 | G | 0.20 | -0.19 | 0.02 | 3.61E-16 | MGC45491 | 117723 | MRPL14 | 124756 | INTERGENIC | 0.98 | 0 |
| rs17400074 | 6 | 44055768 | G | 0.08 | -0.46 | 0.06 | 8.17E-16 | MGC45491 | 20548 | MRPL14 | 133581 | INTERGENIC | 0.44 | 1 |
| rs111968152 | 6 | 43944908 | A | 0.04 | 1.16 | 0.14 | 1.18E-15 | VEGFA | 82709 | MGC45491 | 131406 | INTERGENIC | 0.11 | 1 |
| rs39332536 | 6 | 43944278 | A | 0.04 | 1.15 | 0.14 | 1.43E-15 | VEGFA | 82079 | MGC45491 | 132036 | INTERGENIC | 0.11 | 1 |
| rs6936668 | 6 | 43944048 | C | 0.04 | 1.15 | 0.14 | 1.45E-15 | VEGFA | 81849 | MGC45491 | 132266 | INTERGENIC | 0.11 | 1 |
| rs7832219 | 8 | 106648153 | C | 0.30 | -0.16 | 0.02 | 1.72E-15 | ZFPM2 | 0 | LRP12 | 977809 | INTRONIC | 0.98 | 1 |
| rs47348879 | 8 | 106652300 | G | 0.30 | -0.16 | 0.02 | 1.78E-15 | ZFPM2 | 0 | LRP12 | 981956 | INTRONIC | 0.98 | 1 |
| rs2343592 | 8 | 106641446 | G | 0.30 | -0.16 | 0.02 | 1.98E-15 | ZFPM2 | 0 | LRP12 | 971102 | INTRONIC | 0.97 | 1 |
| rs47348875 | 8 | 106623913 | C | 0.26 | -0.16 | 0.02 | 9.46E-15 | ZFPM2 | 0 | LRP12 | 953569 | INTRONIC | 1.00 | 0 |
| rs168733461 | 8 | 106618857 | C | 0.26 | -0.16 | 0.02 | 1.07E-14 | ZFPM2 | 0 | LRP12 | 948313 | INTRONIC | 0.99 | 1 |
| rs844294 | 6 | 44086685 | C | 0.51 | -0.15 | 0.02 | 1.19E-14 | MGC45491 | 67631 | VEGFA | 146486 | INTRONIC | 0.97 | 1 |
| rs42236085 | 6 | 43971742 | C | 0.38 | -0.43 | 0.06 | 1.27E-14 | MGC45491 | 104574 | VEGFA | 109543 | INTRONIC | 0.12 | 1 |
| rs168733402 | 8 | 106658423 | T | 0.33 | -0.15 | 0.02 | 1.97E-14 | ZFPM2 | 0 | LRP12 | 988079 | INTRONIC | 0.99 | 1 |
| rs910604 | 6 | 44061649 | A | 0.20 | -0.18 | 0.02 | 2.15E-14 | MGC45491 | 14667 | MRPL14 | 127700 | INTERGENIC | 0.98 | 0 |
| rs16873418 | 8 | 106661321 | G | 0.33 | -0.15 | 0.02 | 2.26E-14 | ZFPM2 | 0 | LRP12 | 990977 | INTRONIC | 0.99 | 1 |
| rs6931378 | 6 | 43982797 | A | 0.50 | 0.37 | 0.05 | 7.27E-14 | MGC45491 | 93519 | VEGFA | 120598 | INTRONIC | 0.14 | 1 |
| rs4416670 | 6 | 44058431 | T | 0.55 | 0.13 | 0.02 | 1.47E-12 | MGC45491 | 17885 | MRPL14 | 130918 | INTERGENIC | 0.99 | 0 |
| rs17400077 | 6 | 44057885 | C | 0.56 | 0.13 | 0.02 | 5.21E-12 | MGC45491 | 18431 | MRPL14 | 131464 | INTERGENIC | 0.99 | 1 |
| rs1776704 | 6 | 44057919 | G | 0.56 | 0.13 | 0.02 | 5.36E-12 | MGC45491 | 18397 | MRPL14 | 131430 | INTERGENIC | 0.96 | 1 |
| rs168733865 | 8 | 106627411 | T | 0.21 | -0.16 | 0.02 | 5.66E-12 | ZFPM2 | 0 | LRP12 | 957067 | INTRONIC | 0.96 | 1 |
| rs1776706 | 6 | 44057985 | C | 0.56 | 0.13 | 0.02 | 5.79E-12 | MGC45491 | 18351 | MRPL14 | 131334 | INTERGENIC | 0.92 | 1 |
| rs4320369 | 6 | 44058040 | C | 0.56 | 0.13 | 0.02 | 5.98E-12 | MGC45491 | 18276 | MRPL14 | 131309 | INTERGENIC | 0.97 | 1 |
| rs17400079 | 6 | 44059217 | T | 0.56 | 0.13 | 0.02 | 6.02E-12 | MGC45491 | 17099 | MRPL14 | 130132 | INTERGENIC | 0.97 | 1 |
| rs910612 | 6 | 44058684 | T | 0.44 | -0.13 | 0.02 | 6.07E-12 | MGC45491 | 17632 | MRPL14 | 130665 | INTERGENIC | 0.96 | 1 |
| rs910613 | 6 | 44058614 | T | 0.56 | 0.13 | 0.02 | 6.10E-12 | MGC45491 | 17702 | MRPL14 | 130735 | INTERGENIC | 0.97 | 1 |
| rs910614 | 6 | 44058596 | T | 0.44 | -0.13 | 0.02 | 6.12E-12 | MGC45491 | 17720 | MRPL14 | 130753 | INTERGENIC | 0.97 | 1 |
| rs7013321 | 8 | 106622734 | A | 0.48 | -0.14 | 0.02 | 6.75E-12 | ZFPM2 | 0 | LRP12 | 957067 | INTRONIC | 0.83 | 1 |
| rs6993696 | 8 | 106650460 | A | 0.46 | -0.13 | 0.02 | 8.54E-12 | ZFPM2 | 0 | LRP12 | 980116 | INTRONIC | 0.99 | 1 |
| rs4741755 | 9 | 2657929 | C | 0.30 | -0.23 | 0.03 | 2.26E-11 | VLDLR | 13444 | KCNV2 | 49596 | INTRONIC | 0.37 | 1 |
| rs16873287 | 8 | 106597151 | G | 0.30 | -0.13 | 0.02 | 5.13E-11 | ZFPM2 | 0 | LRP12 | 926807 | INTRONIC | 1.02 | 0 |

FIG. 6C

| SNP | Chr | Position | CA | CAF | beta | SE | p | Gene 1 | Distance | Gene 2 | Distance | Function | O/E ratio | Imputed |
|---|---|---|---|---|---|---|---|---|---|---|---|---|---|---|
| rs16873291 | 8 | 106597206 | T | 0.30 | -0.13 | 0.02 | 5.30E-11 | ZFPM2 | 0 | LRP12 | 926862 | INTRONIC | 1.02 | 0 |
| rs12676726 | 8 | 106597884 | C | 0.30 | -0.13 | 0.02 | 5.44E-11 | ZFPM2 | 0 | LRP12 | 927540 | INTRONIC | 1.01 | 1 |
| rs9472147 | 6 | 43944737 | A | 0.17 | -0.49 | 0.07 | 5.78E-11 | VEGFA | 62538 | MGC45491 | 131579 | INTERGENIC | 0.12 | 1 |
| rs10105733 | 8 | 106595037 | G | 0.29 | -0.14 | 0.02 | 6.09E-11 | ZFPM2 | 0 | LRP12 | 924693 | INTRONIC | 1.01 | 1 |
| rs4734119 | 8 | 106599699 | G | 0.30 | -0.13 | 0.02 | 7.33E-11 | ZFPM2 | 0 | LRP12 | 929355 | INTRONIC | 1.01 | 0 |
| rs1157141 | 8 | 106600486 | G | 0.30 | -0.13 | 0.02 | 7.33E-11 | ZFPM2 | 0 | LRP12 | 930142 | INTRONIC | 1.01 | 1 |
| rs1157142 | 8 | 106600850 | A | 0.30 | -0.13 | 0.02 | 7.34E-11 | ZFPM2 | 0 | LRP12 | 930506 | INTRONIC | 1.01 | 1 |
| rs6996138 | 8 | 106601653 | G | 0.30 | -0.13 | 0.02 | 7.35E-11 | ZFPM2 | 0 | LRP12 | 931309 | INTRONIC | 1.01 | 1 |
| rs4734873 | 8 | 106602506 | A | 0.30 | -0.13 | 0.02 | 7.36E-11 | ZFPM2 | 0 | LRP12 | 932162 | INTRONIC | 1.01 | 0 |
| rs7001868 | 8 | 106602795 | G | 0.30 | -0.13 | 0.02 | 7.38E-11 | ZFPM2 | 0 | LRP12 | 932451 | INTRONIC | 1.01 | 1 |
| rs10094510 | 8 | 106592361 | A | 0.29 | -0.13 | 0.02 | 8.33E-11 | ZFPM2 | 0 | LRP12 | 922017 | INTRONIC | 1.01 | 0 |
| rs7007968 | 8 | 106591021 | G | 0.29 | -0.13 | 0.02 | 9.27E-11 | ZFPM2 | 0 | LRP12 | 920677 | INTRONIC | 1.02 | 1 |
| rs16873231 | 8 | 106587411 | G | 0.29 | -0.13 | 0.02 | 1.36E-10 | ZFPM2 | 0 | LRP12 | 917067 | INTRONIC | 1.02 | 1 |
| rs6997293 | 8 | 106587104 | C | 0.29 | -0.13 | 0.02 | 1.47E-10 | ZFPM2 | 0 | LRP12 | 916760 | INTRONIC | 1.01 | 1 |
| rs1868650 | 8 | 106587088 | C | 0.29 | -0.13 | 0.02 | 1.52E-10 | ZFPM2 | 0 | LRP12 | 916744 | INTRONIC | 1.01 | 1 |
| rs1868649 | 8 | 106587041 | A | 0.29 | -0.13 | 0.02 | 1.57E-10 | ZFPM2 | 0 | LRP12 | 916697 | INTRONIC | 1.01 | 1 |
| rs2291192 | 8 | 106586248 | A | 0.29 | -0.13 | 0.02 | 1.77E-10 | ZFPM2 | 0 | LRP12 | 915904 | INTRONIC | 1.01 | 1 |
| rs12678719 | 8 | 106585230 | G | 0.43 | -0.12 | 0.02 | 1.95E-10 | ZFPM2 | 0 | LRP12 | 914886 | INTRONIC | 0.99 | 0 |
| rs10093110 | 8 | 106634590 | A | 0.29 | -0.13 | 0.02 | 2.18E-10 | ZFPM2 | 0 | LRP12 | 964246 | INTRONIC | 1.01 | 1 |
| rs6968664 | 8 | 106582477 | G | 0.29 | -0.13 | 0.02 | 2.33E-10 | ZFPM2 | 0 | LRP12 | 912133 | INTRONIC | 1.01 | 0 |
| rs4734869 | 8 | 106582004 | A | 0.29 | -0.13 | 0.02 | 2.60E-10 | ZFPM2 | 0 | LRP12 | 911660 | INTRONIC | 1.01 | 1 |
| rs910611 | 6 | 44058829 | C | 0.08 | -0.26 | 0.04 | 2.61E-10 | MGC45491 | 17487 | MRPL14 | 130520 | INTERGENIC | 0.77 | 1 |
| rs748785 | 9 | 2684347 | C | 0.13 | 0.24 | 0.04 | 1.01E-09 | KCNV2 | 23178 | VLDLR | 39862 | INTERGENIC | 0.52 | 1 |
| rs7767854 | 6 | 44065304 | T | 0.11 | -0.22 | 0.04 | 1.02E-09 | MGC45491 | 11012 | MRPL14 | 124045 | INTERGENIC | 0.74 | 1 |
| rs6995272 | 8 | 106662838 | T | 0.46 | 0.14 | 0.02 | 1.98E-09 | ZFPM2 | 0 | LRP12 | 992494 | INTRONIC | 0.66 | 1 |
| rs12675041 | 8 | 106598221 | A | 0.34 | -0.12 | 0.02 | 2.10E-09 | ZFPM2 | 0 | LRP12 | 927877 | INTRONIC | 0.96 | 1 |
| rs1740080 | 6 | 44060390 | A | 0.12 | -0.18 | 0.03 | 2.76E-09 | MGC45491 | 15926 | MRPL14 | 128959 | INTERGENIC | 0.93 | 1 |
| rs910606 | 6 | 44061307 | A | 0.12 | -0.18 | 0.03 | 2.90E-09 | MGC45491 | 15009 | MRPL14 | 128042 | INTERGENIC | 0.94 | 0 |
| rs1631662 | 6 | 44061336 | T | 0.12 | -0.18 | 0.03 | 2.93E-09 | MGC45491 | 14980 | MRPL14 | 128013 | INTERGENIC | 0.94 | 1 |
| rs2051074 | 6 | 44056431 | T | 0.04 | -0.41 | 0.07 | 5.80E-09 | MGC45491 | 19885 | MRPL14 | 132918 | INTERGENIC | 0.46 | 1 |
| rs9381262 | 6 | 43983427 | A | 0.45 | -0.29 | 0.05 | 6.78E-09 | MGC45491 | 92689 | VEGFA | 121228 | INTERGENIC | 0.14 | 1 |
| rs1450163 | 8 | 106601298 | C | 0.37 | -0.11 | 0.02 | 1.11E-08 | ZFPM2 | 0 | LRP12 | 930954 | INTRONIC | 1.00 | 1 |

FIG. 6D

| SNP | Chr | Position | CA | CAF | beta | SE | p | Gene 1 | Distance | Gene 2 | Distance | Function | O/E ratio | Imputed |
|---|---|---|---|---|---|---|---|---|---|---|---|---|---|---|
| rs78364542 | 8 | 106603619 | T | 0.37 | -0.11 | 0.02 | 1.13E-08 | ZFPM2 | 0 | LRP12 | 933275 | INTRONIC | 1.01 | 0 |
| rs16897113 | 6 | 44076194 | T | 0.03 | 0.62 | 0.11 | 1.34E-08 | MGCA5491 | 122 | MRPL14 | 113155 | UPSTREAM | 0.29 | 1 |
| rs2343595 | 8 | 106660383 | G | 0.45 | -0.11 | 0.02 | 2.26E-08 | ZFPM2 | 0 | LRP12 | 990039 | INTRONIC | 1.01 | 1 |
| rs16873415 | 8 | 106660978 | G | 0.45 | -0.11 | 0.02 | 2.39E-08 | ZFPM2 | 0 | LRP12 | 990634 | INTRONIC | 1.01 | 0 |
| rs1901061 | 8 | 106619426 | A | 0.39 | 0.11 | 0.02 | 3.08E-08 | ZFPM2 | 0 | LRP12 | 949082 | INTRONIC | 0.94 | 1 |
| rs13493319 | 8 | 106625810 | A | 0.39 | 0.11 | 0.02 | 3.59E-08 | ZFPM2 | 0 | LRP12 | 955466 | INTRONIC | 0.94 | 1 |
| rs9369430 | 6 | 43942229 | G | 0.16 | 0.24 | 0.04 | 3.68E-08 | VEGFA | 80030 | MGCA5491 | 134087 | INTERGENIC | 0.33 | 1 |
| rs748786 | 9 | 2684436 | T | 0.12 | 0.23 | 0.04 | 3.91E-08 | KCNV2 | 23089 | VLDLR | 39951 | INTERGENIC | 0.52 | 1 |
| rs4734122 | 8 | 106629546 | A | 0.41 | 0.11 | 0.02 | 4.15E-08 | ZFPM2 | 0 | LRP12 | 959202 | INTRONIC | 0.99 | 1 |
| rs1375955 | 8 | 106624215 | T | 0.39 | 0.11 | 0.02 | 4.30E-08 | ZFPM2 | 0 | LRP12 | 953871 | INTRONIC | 0.94 | 1 |
| rs126679049 | 8 | 106598022 | G | 0.22 | -0.12 | 0.02 | 4.75E-08 | ZFPM2 | 0 | LRP12 | 927678 | INTRONIC | 0.99 | 0 |

CA: coded allele; CAF: coded allele frequency; Chr: chromosome; KCNV2: potassium voltage-gated channel subfamily V, member 2; LRP12: low-density lipoprotein receptor-related protein gene; MCG45491: uncharacterized protein, also known as C6orf223; MRPL14: mitochondrial ribosomal protein L14; O/E ratio: observed over expected ratio (measuring imputation accuracy); p: p-value; SE: standard error; SNP: single nucleotide polymorphism; VEGF: vascular endothelial growth factor; VLDLR: very low density lipoprotein receptor; ZFPM2: zinc finger protein, multitype 2.

FIG. 6E

| SNP | Chr | Position | Function | CAF | Coded Allele | strand | beta (FHS) | SE (FHS) | p (FHS) | p (PIVUS) | p (SFS) | Dir | Meta-p (FHS+PIVUS) | Meta-p (all) | Gene1 | Distance (kb) | Gene2 | Distance (kb) |
|---|---|---|---|---|---|---|---|---|---|---|---|---|---|---|---|---|---|---|
| rs6921438 | 6 | 44033585 | intergenic | 0.51 | G | + | 0.72 | 0.01 | 6.11x10⁻⁵⁹⁶ | NA | 2.93x10⁻³⁰ | -? | 6.11x10⁻⁵⁹⁶ | 4.44x10⁻⁶³¹ | MGC45491 | 42.7 | MRPL14 | 155.8 |
| rs4513773 | 6 | 44033504 | intergenic | 0.47 | G | + | -0.70 | 0.01 | 2.08x10⁻⁵⁶³ | 6.23x10⁻¹²⁵ | NA | ++? | 4.45x10⁻⁶¹³ | 1.10x10⁻⁶⁴⁴ | MGC45491 | 42.8 | MRPL14 | 155.8 |
| rs9472159 | 6 | 44027673 | intergenic | 0.50 | C | + | 0.76 | 0.02 | 4.30x10⁻⁴⁵² | 3.27x10⁻¹⁰⁴ | 4.11x10⁻²⁵ | --- | 1.61x10⁻⁵⁵⁷ | 8.16x10⁻⁵⁸³ | MGC45491 | 48.6 | MRPL14 | 161.7 |
| rs9369434 | 6 | 44026385 | intergenic | 0.53 | C | + | 0.84 | 0.02 | 2.15x10⁻⁴¹² | 1.43x10⁻⁸⁵ | 5.31x10⁻²⁰ | --- | 1.43x10⁻⁴⁹⁶ | 1.21x10⁻¹⁰⁴ | MGC45491 | 49.9 | MRPL14 | 163.0 |
| rs1776717 | 6 | 44059314 | intergenic | 0.21 | A | + | -0.23 | 0.02 | 8.10x10⁻²⁰ | 3.74x10⁻⁴ | 9.75x10⁻⁶ | --- | 3.28x10⁻²² | 1.07x10⁻²⁶ | MGC45491 | 17.0 | MRPL14 | 130.0 |
| rs1776721 | 6 | 43998961 | 3'UTR | 0.31 | T | + | -0.18 | 0.02 | 1.52x10⁻¹⁹ | 3.43x10⁻⁴ | 0.02 | --- | 5.38x10⁻²³ | 4.23x10⁻²⁵ | MGC45491 | 77.3 | VEGF | 136.8 |
| rs1866979 | 6 | 44112879 | 3'UTR | 0.41 | G | + | 0.17 | 0.02 | 3.71x10⁻¹⁹ | 3.23x10⁻⁵ | 0.01 | +++ | 6.55x10⁻²¹ | 1.70x10⁻²¹ | MGC45491 | 63.4 | VEGF | 150.7 |
| rs9472155 | 6 | 44005705 | intronic | 0.22 | T | + | -0.20 | 0.02 | 4.45x10⁻¹⁹ | 3.93x10⁻⁹ | 0.01 | --- | 2.50x10⁻²⁴ | 1.51x10⁻²⁶ | MGC45491 | 70.6 | VEGF | 143.6 |
| rs844294 | 6 | 44008685 | intronic | 0.52 | C | + | -0.15 | 0.02 | 1.18x10⁻¹⁴ | 2.25x10⁻⁵ | 0.09 | --- | 1.41x10⁻¹⁸ | 2.46x10⁻¹⁹ | MGC45491 | 67.6 | VEGF | 146.5 |
| rs4416670 | 6 | 44058431 | intronic | 0.55 | T | + | 0.13 | 0.02 | 1.47x10⁻¹³ | 0.10 | 2.87x10⁻⁴ | +++ | 1.44x10⁻¹² | 2.08x10⁻¹⁵ | MGC45491 | 17.9 | MRPL14 | 130.9 |
| rs910611 | 6 | 44058829 | intergenic | 0.08 | C | + | -0.26 | 0.04 | 2.61x10⁻¹³ | 6.36x10⁻⁶ | 0.11 | --- | 9.82x10⁻¹⁵ | 1.94x10⁻¹⁴ | MGC45491 | 17.5 | MRPL14 | 130.5 |
| rs6993770 | 8 | 106650704 | intronic | 0.32 | T | + | -0.17 | 0.02 | 2.50x10⁻¹⁴ | 3.99x10⁻⁶ | 0.02 | --- | 2.60x10⁻²² | 4.71x10⁻²³ | ZFPM2 | 0 | LRP12 | 980.4 |
| rs16873402 | 8 | 106656423 | intronic | 0.33 | T | + | -0.15 | 0.02 | 1.97x10⁻¹⁴ | 9.49x10⁻⁸ | 0.16 | --- | 1.10x10⁻²⁰ | 5.32x10⁻²⁰ | ZFPM2 | 0 | LRP12 | 988.1 |
| rs16873365 | 8 | 106627411 | intronic | 0.22 | T | + | -0.16 | 0.02 | 5.85x10⁻¹³ | 2.08x10⁻⁷ | 0.37 | --- | 4.10x10⁻¹⁶ | 2.27x10⁻¹⁵ | ZFPM2 | 0 | LRP12 | 957.1 |
| rs7013321 | 8 | 106662734 | intronic | 0.49 | A | + | -0.14 | 0.02 | 6.75x10⁻¹³ | NA | 0.01 | -?- | 6.75x10⁻¹³ | 4.49x10⁻¹³ | ZFPM2 | 0 | LRP12 | 992.4 |
| rs6993696 | 8 | 106650460 | intronic | 0.46 | A | + | -0.13 | 0.02 | 8.54x10⁻¹² | 1.49x10⁻⁴ | 0.05 | --- | 6.18x10⁻¹⁶ | 2.12x10⁻¹⁶ | ZFPM2 | 0 | LRP12 | 980.1 |
| rs16873291 | 8 | 106597206 | intronic | 0.31 | T | + | -0.13 | 0.02 | 5.30x10⁻¹¹ | 7.65x10⁻⁷ | 0.07 | --- | 1.12x10⁻¹⁵ | 4.75x10⁻¹⁶ | ZFPM2 | 0 | LRP12 | 926.9 |
| rs1343319 | 8 | 106625810 | intronic | 0.39 | A | + | 0.11 | 0.02 | 3.59x10⁻⁸ | 1.32x10⁻² | 0.05 | +++ | 1.99x10⁻¹⁰ | 3.53x10⁻¹¹ | ZFPM2 | 0 | LRP12 | 955.5 |
| rs10738760 | 9 | 2681185 | intergenic | 0.49 | A | + | 0.28 | 0.02 | 1.96x10⁻³⁴ | 1.12x10⁻⁸ | 0.03 | +++ | 4.46x10⁻⁴¹ | 9.93x10⁻⁴⁰ | KCNV2 | 26.3 | VLDLR | 36.7 |
| rs4478920 | 9 | 2663933 | intergenic | 0.36 | A | + | -0.24 | 0.02 | 3.76x10⁻²² | 2.40x10⁻⁸ | 0.02 | --- | 6.11x10⁻²⁸ | 7.93x10⁻²⁸ | VLDLR | 19.4 | KCNV2 | 43.6 |
| rs4741756 | 9 | 2658187 | intergenic | 0.28 | C | + | -0.25 | 0.02 | 2.95x10⁻²¹ | 8.64x10⁻⁶ | 0.09 | --- | 4.45x10⁻²⁴ | 3.41x10⁻²² | VLDLR | 13.7 | KCNV2 | 49.3 |
| rs2375980 | 9 | 2682622 | intergenic | 0.42 | G | + | -0.25 | 0.02 | 1.30x10⁻²⁷ | 2.25x10⁻⁸ | 0.02 | --- | 2.55x10⁻³⁴ | 1.01x10⁻³³ | KCNV2 | 24.9 | VLDLR | 38.1 |
| rs10122587 | 9 | 2681951 | intergenic | 0.28 | T | + | -0.22 | 0.02 | 3.02x10⁻²⁴ | NA | 0.02 | -?- | 3.02x10⁻²⁴ | 4.67x10⁻²⁴ | KCNV2 | 25.6 | VLDLR | 37.5 |
| rs10967492 | 9 | 2671175 | intergenic | 0.21 | A | + | -0.22 | 0.02 | 1.02x10⁻²⁰ | NA | 0.10 | -?- | 1.02x10⁻²⁰ | 1.25x10⁻²⁰ | VLDLR | 26.7 | KCNV2 | 36.3 |
| rs10967470 | 9 | 2665698 | intergenic | 0.24 | G | + | -0.22 | 0.02 | 1.17x10⁻²¹ | NA | 0.04 | -?+ | 1.17x10⁻²¹ | 2.79x10⁻²¹ | VLDLR | 21.2 | KCNV2 | 41.8 |

CAF: Coded Allele Frequency; Chr: chromosome; Dir: Direction of association in FHS, PIVUS, SFS; Gene1: closest referenced gene; Gene2: second closest referenced gene; Meta-p: meta-analysis p-value; SNP: Single Nucleotide Polymorphism; CSE: Standard Error; *genome build 36.3; †effect estimate for the minor allele; ‡inverse variance meta-analysis; §effective sample size weighted meta-analysis; ¶model A: adjusted for age and gender, as well as for the ninth principal component in FHS

FIG. 7

IDENTIFICATION OF GENETIC VARIANTS

RELATED APPLICATIONS

The present application is a divisional of U.S. application Ser. No. 13/594,721, filed Aug. 24, 2012, which claims the benefit of U.S. Provisional Application No. 61/527,531 filed on Aug. 25, 2011. The entireties of which are incorporated herein by reference.

TECHNICAL FIELD

This disclosure relates to the identification of allelic variation within single nucleotide polymorphisms that can be used to determine susceptibility to VEGF-based therapy.

BACKGROUND

Vascular endothelial growth factor (VEGF, also referred to as VEGFA in contrast to other members of the VEGF family) is pivotal in many physiological and pathological processes. It is primarily known for its key role in the stimulation of angiogenesis, with a potent mitogenic effect on vascular endothelial cells from arteries, veins and lymphatics. VEGF also promotes vasodilatation by inducing the production of nitric oxide and prostacyclin by endothelial cells. In addition, VEGF is involved in hematopoietic development and chemotaxis of monocytes, regulation of osteoclast differentiation, stimulation of surfactant production, and has neurotrophic and neuroprotective effects on neuronal and glial cells. Elevated circulating VEGF levels have been observed in vascular disease (ischemic heart disease, heart failure, stroke), and in various other disorders, including diabetes, cognitive decline and dementia, reproductive, immune-inflammatory disorders, and neoplastic diseases. Administration of VEGF promotes angiogenesis in patients with critical leg ischemia, as well as in animal models of coronary and limb ischemia. VEGF inhibitors such as bevacizumab and sorafenib have been successfully used to inhibit angiogenesis in several tumors, in macular degeneration and in rheumatoid arthritis.

However, despite the considerable toxicity associated with VEGF inhibitor drugs, to date there have been no pharmacogenomic studies to identify potential sub-groups of responders partly because the genetic determinants of VEGF concentrations remain poorly understood.

Indeed, although the heritability of circulating VEGF levels is very high, ranging between 60 and 80%, few studies have assessed the relationship between circulating VEGF levels and genetic variants.

Candidate gene studies exploring associations between VEGF polymorphisms and circulating VEGF levels have yielded controversial results. Eight studies have found significant associations with candidate polymorphisms (rs699947, rs1570360, rs833061, rs2010963, rs3025039 and −2549 18 bp I/D) in the promoter, 5' and 3' untranslated region of the VEGF gene. However, several other studies did not identify any association with these and other VEGF SNPs.

While several studies have examined the association of candidate genetic variants with VEGF gene expression in pathological tissues, little is known about the genetic variants influencing VEGF expression in normal cells.

Therefore, there is a need for greater understanding of polymorphisms linked to VEGF levels, in order to identify patients who are more likely to respond favorably to anti-VEGF and pro-angiogenic VEGF based treatments. Such therapies can have major side-effects, and optimizing the risk to benefit ratio of their administration could lead to substantial improvements in patient care.

SUMMARY

According to a first aspect, the present disclosure provides a method for identifying whether a subject is likely to be more or less responsive to VEGF-based therapy, comprising screening a nucleic acid sample obtained from the subject to provide output information which identifies the presence or absence of an allelic variant, wherein the allelic variant is selected from the group consisting of: (i) rs6921438; (ii) rs4416670; (iii) rs6993770; and (iv) rs10738760, and wherein the presence or absence of the allelic variant indicates that the subject is likely to be more or less likely to be responsive to VEGF based therapy.

According to a second aspect, the present disclosure provides a method for identifying whether a subject is likely to be more or less responsive to VEGF-based therapy, comprising screening a nucleic acid sample obtained from the subject to provide output information which identifies the presence or absence of at least one allelic variant associated with VEGF mRNA, wherein the at least one allelic variant is selected from the group consisting of: (i) rs16873365; (ii) rs16873402; (iii) rs6993770; (iv) rs16873291; (v) rs2375980; and (vi) rs910611, wherein the presence or absence of the allelic variant indicates that the subject is more or less likely to be responsive to VEGF-based therapy.

According to a third aspect, the present disclosure provides a method for identifying whether a subject is likely to be more or less responsive to VEGF-based therapy, comprising screening a sample obtained from a subject to determine the level of expression of one or more of the VLDLR, LRP12, ZFPM2 and KCNV2 genes, and comparing against a control value, wherein an increase in expression compared to the control indicates that the patient is more or less likely to be responsive to VEGF or anti-VEGF therapy.

According to a fourth aspect, the present disclosure provides a method for identifying molecules that affect the level of circulating VEGF in a subject, comprising screening a target molecule to provide output information to establish whether the molecule affects the activity of the product of any of the VLDLR, LRP12, ZFPM2 and KCNV2 genes, wherein a molecule that inhibits the activity will alter the level of circulating VEGF in vivo.

According to a fifth aspect, the present disclosure provides a method for administering a VEGF-based therapy to a subject, the method comprising the step of screening a nucleic acid sample obtained from the subject to provide output information which identifies the presence or absence of an allelic variant, wherein the allelic variant is selected from the group consisting of: (i) rs6921438, (ii) rs4416670, (iii) rs6993770, and (iv) rs10738760, wherein if the nucleic acid sample is screened for the allelic variant rs6921438 and a guanine residue is detected at base 323 of SEQ ID No. 1 at one or both alleles, a VEGF-based therapy is administered, wherein if the nucleic acid sample is screened for the allelic variant rs4416670 and a thymine residue is detected at base 221 of SEQ ID No. 2 at one or both alleles, a VEGF-based therapy is administered, wherein if the nucleic acid sample is screened for the allelic variant rs6993770 and a thymine residue is detected at base 235 of SEQ ID No. 3 at one or both alleles, a VEGF-based therapy is not administered, wherein if the nucleic acid sample is screened for the allelic variant rs10738760 and a guanine residue is detected at base 201 of SEQ ID No. 4 at one or both alleles, a VEGF-based therapy is administered.

According to a sixth aspect, the present disclosure provides an array comprising one or more reagents deposited on a substrate, wherein the reagents have affinity for and/or hybridize to, one or more polynucleotides comprising single nucleotide polymorphisms identified herein as rs6921438, rs4416670, rs6993770, rs10738760, rs16873365, rs16873402, rs16873291, rs2375980, rs910611 and/or wherein the reagents have affinity for and/or hybridize to one or more of the genes selected from VLDLR, LRP12, ZFPM2 and KCNV2.

BRIEF DESCRIPTION OF THE FIGURES

FIGS. 6A-6E is a single table showing certain properties of SNPs identified by genome-wide genotyping.

FIG. 7 is a table showing selected properties of SNPs identified by genome-wide genotyping.

DETAILED DESCRIPTION

Figure 1:
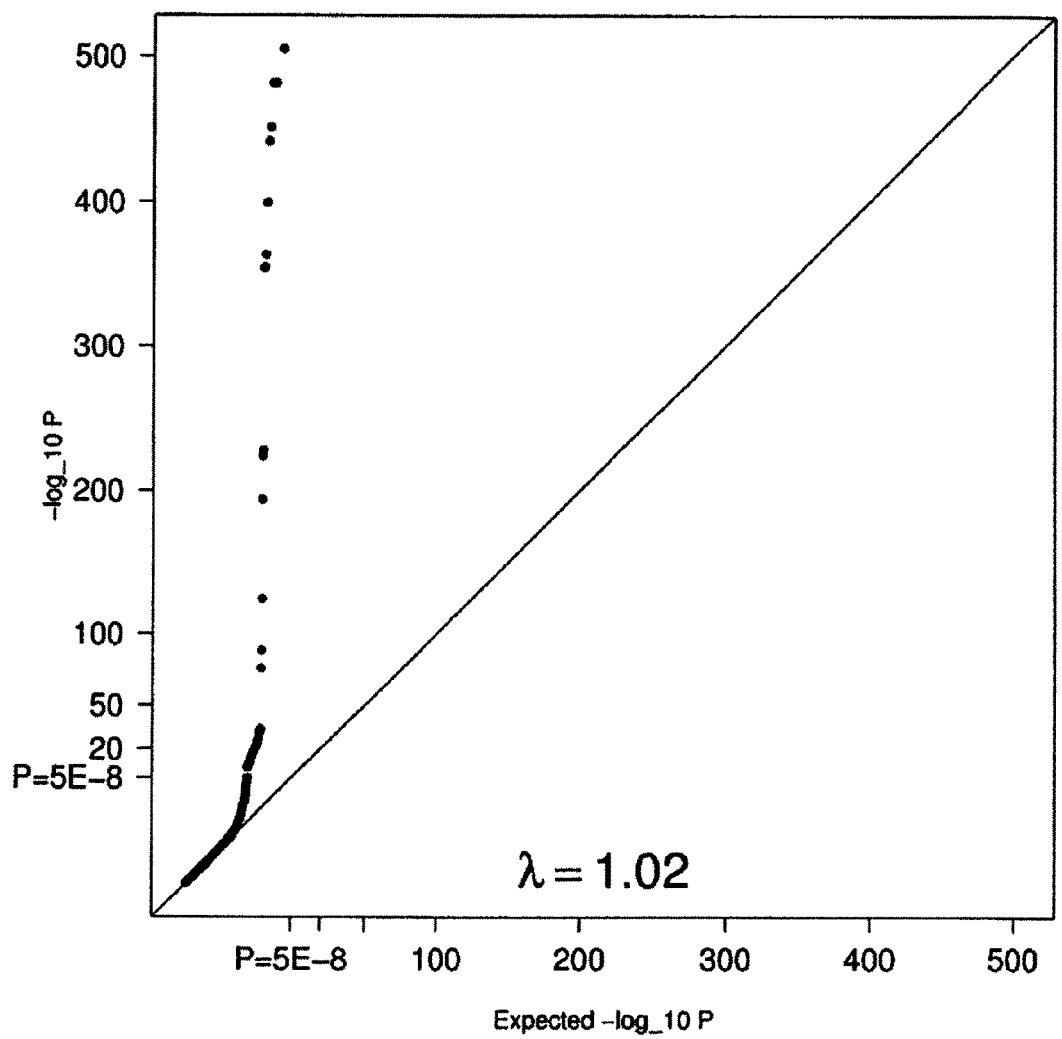
FIG. 1 is a QQ-plot showing the observed versus the expected p-values after meta-analysis for serum VEGF levels (the solid line shows the distribution under the null-hypothesis).

The present disclosure is based on the identification of novel genetic variants associated with circulating VEGF levels, on chromosomes 6, 8 and 9. In particular, four single nucleotide polymorphisms (SNPs) have been identified that play a key role in determining serum VEGF levels. These SNPs are: rs6921438; rs4416670; rs6993770; and rs10738760. Allelic variation in these four SNPs has been found to account for approximately 48% of the heritability of serum VEGF levels. Allelic variation at a single SNP, rs6921438, has been found to account for approximately 42% of phenotypic variance in serum VEGF levels. Determining genetic variation at these SNPs enables clinicians to identify patients who are more likely to respond favorably to anti-VEGF and/or pro-angiogenic VEGF-based treatments.

rs6921438 is located on chromosome 6p21.1 and is identified herein as base 323 of SEQ ID No. 1. The wild-type nucleotide at this position is adenine (A) (coded allele frequency 0.49); however the presence of guanine (G) (coded allele frequency 0.51) instead of adenine is indicative of increased association with VEGF. As such, those subjects having G at this position are more likely to respond favorably to VEGF-based treatment, in particular, anti-VEGF therapies.

rs4416670 is located on chromosome 6p21.1 and is identified herein as base 221 of SEQ ID NO. 2. The wild-type nucleotide at this position is cytosine (C) (coded allele frequency 0.45); however the presence of thymine (T) (coded allele frequency 0.55) instead of cytosine is indicative of increased association with VEGF. As such, those subjects having T at this position are more likely to respond favorably to VEGF-based treatment.

rs6993770 is located on chromosome 8q23.1 and is identified herein as base 235 of SEQ ID No. 3. The wild-type nucleotide at this position is adenine (A) (coded allele frequency 0.68). The presence of thymine (T) (coded allele frequency 0.32) instead of adenine is indicative of decreased association with VEGF. As such, those subjects having T at this position are less likely to respond favorably to VEGF-based treatment.

rs10738760 is located on chromosome 9p24.2 and is identified herein as base 201 of SEQ ID NO. 4. The wild-type nucleotide at this position is adenine (A) (coded allele frequency 0.49); however the presence of guanine (G) (coded allele frequency 0.51) instead of adenine is indicative of increased association with VEGF. As such, those subjects having G at this position are more likely to respond favorably to VEGF-based treatment.

Accordingly, a first aspect of the present disclosure provides a method for identifying whether a subject is more or less likely to be responsive to VEGF or anti-VEGF therapy, comprising screening a nucleic acid sample obtained from the subjects for the presence or absence of an allelic variant, wherein the allelic variant is selected from the group consisting of: (i) rs6921438; (ii) rs4416670; (iii) rs6993770; and (iv) rs10738760, and wherein the presence or absence of the allelic variant indicates that the subject is more or less likely to be responsive VEGF-based therapy.

The present disclosure is useful when considering a VEGF-based therapy for a patient suffering from a disease or condition that is associated with high or low circulating VEGF levels. Prior to administering a VEGF-based therapy, a patient can be screened to determine how responsive they are likely to be to the VEGF-based therapy. In this context, the method of the disclosure could be used to screen a patient requiring pro-VEGF therapy (for example, to promote angiogenesis to treat ischemia) or, alternatively, to screen a patient requiring anti-VEGF therapy (for example, for the treatment of a tumor). The methods of the disclosure are equally applicable to both cases. However, in a preferred embodiment the patient has a condition that can be treated by administering anti-VEGF drugs, and therefore the method of the disclosure is used to screen for the likelihood that the patient will be responsive to anti-VEGF therapy.

As used herein, the term "VEGF-based therapy" refers to treatments and/or drugs which inhibit or promote VEGF activity. Therefore, "VEGF-based therapy" includes both anti-VEGF therapies and pro-VEGF therapies. Examples of anti-VEGF drugs (also known as VEGF-inhibitors) include bevacizumab (Avastin™), ranibizumab (Lucentis™), lapatinib (Tykerb™), sunitinib (Sutent™), sorafenib (Nexavar™), axitinib, pazopanib and thiazolidinediones. Pro-VEGF therapies enhance the activity or function of VEGF and are used clinically to promote angiogenesis.

The nucleic acid sample can be isolated from a biological sample, such as a blood sample, taken from a patient. The skilled person will be familiar with conventional techniques for obtaining isolated nucleic acid samples from individual subjects. As used herein, the term "screening" refers to carrying out an assay to identify allelic variation at specified locations within the subject's genome. Preferably, the screening step takes place in vitro.

Furthermore, six SNPs have been identified as being associated with VEGF mRNA levels. These SNPs are summarized in Table 5.

rs16873365 is located on chromosome 8 and is identified herein as base 251 of SEQ ID No. 5.

rs16873402 is located on chromosome 8 and is identified herein as base 251 of SEQ ID No. 6.

rs6993770 is located on chromosome 8 and is identified herein as base 235 of SEQ ID No. 3. As described above, this SNP is also associated with VEGF peptide levels.

rs16873291 is located on chromosome 8 and is identified herein as base 251 of SEQ ID No. 7.

rs2375980 is located on chromosome 9 and is identified herein as base 501 of SEQ ID No. 8. The wild-type nucleotide at this position is guanine (G) (coded allele frequency 0.42).

rs910611 is located on chromosome 6 and is identified herein as base 301 of SEQ ID No. 9.

Therefore, according to a second aspect of this disclosure, a method for identifying whether a subject is more or less likely to be responsive to VEGF-based therapy comprises screening a nucleic acid sample obtained from the subjects for the presence or absence of at least one allelic variant associated with VEGF mRNA, wherein the at least one allelic variant is selected from the group consisting of: (i) rs16873365; (ii) rs16873402; (iii) rs6993770; (iv) rs16873291; (v) rs2375980; and (vi) rs910611, wherein the presence or absence of the allelic variant indicates that the subject is more or less likely to be responsive to VEGF-based therapy.

According to a third aspect of the present disclosure, a method for identifying whether a subject is more or less likely to be responsive to VEGF-based therapy, comprises determining the level of expression of one or more of the VLDLR, LRP12, ZFPM2 and KCNV2 genes in a sample obtained from a patient, and comparing against a control value, wherein an increase in expression compared to the control indicates that the subject is more or less likely to be responsive to VEGF-based therapy.

VLDLR (Very low-density lipoprotein receptor) is located at chromosomal position 9p24 and is identified by the Human Gene Nomenclature Committee as HGNC: 12698.

LRP12 (Low-density lipoprotein receptor-related protein 12) is located at chromosomal position 8q22.2 and is identified by the Human Gene Nomenclature Committee as HGNC:31708.

ZFPM2 (Zinc finger protein ZFPM2) is located at chromosomal position 8q23 and is identified by the Human Gene Nomenclature Committee as HGNC:16700.

KCNV2 (Potassium voltage-gated channel subfamily V member 2) is located at chromosomal position 9p24.2 and is identified by the Human Gene Nomenclature Committee as HGNC:19698.

As used herein the term "expression level" refers to the amount of a specified protein (or mRNA coding for the protein) in a patient's sample. The expression level is then compared to that of a control sample.

Methods of measuring the level of expression of a protein from a biological sample are well known in the art and any suitable method may be used. Protein or nucleic acid from the sample may be analyzed to determine the expression level. An example of a suitable method is a quantitative PCR reaction or mRNA (or cDNA) obtained from the patient's sample. The use of quantitative PCR to detect gene expression levels is well known in the art. Kits for quantitative PCR-based gene expression analysis are commercially available, for example the Quantitect system manufactured by Qiagen. Simultaneous analysis of expression levels in multiple samples using a hybridization-based nucleic acid array system is well known in the art and is also within the scope of the disclosure.

Preferably, the expression level of specific gene products is quantified in terms of "standardized abundance", which provides a numerical value that takes into account natural variation in the concentration of a given protein in a biological sample. The standardized abundance value enables comparison with a known control value.

In one embodiment, the methods of the first, second and/or third aspects of the disclosure can be combined, such that a patient sample is screened for the presence or absence of one or more allelic variants and the expression level of one or more of the genes VLDLR, LRP12, ZFPM2 and KCNV2 is also determined. The output information from these methods is combined to provide an overall output corresponding to likelihood of responsiveness to VEGF-based therapy.

According to a fourth aspect of the present disclosure, a method for identifying molecules that affect the level of circulating VEGF in a subject comprises screening a target molecule to establish whether it affects (i.e. inhibits or enhances) the activity of the product of any of the VLDLR, LRP12, ZFPM2 and KCNV2 genes, wherein a molecule that affects the activity will alter (increase or decrease) the level of circulating VEGF in vivo.

As used in the context of the fourth aspect, the term "screening" refers to carrying out an assay to identify whether a target molecule affects the activity of one or more of the genes specified. Preferably, the screening step takes place in vitro.

The terms "circulating VEGF levels" and "serum VEGF levels" are used interchangeably herein.

The terms "subject" and "patient" are used interchangeably throughout this description and refer to an animal, preferably a mammal, and most preferably a human. Preferably, the subject has a disease or condition that may be treated using VEGF-based therapy.

According to a fifth aspect, the present disclosure provides a method for administering a VEGF-based therapy to a subject, the method comprising the step of screening a nucleic acid sample obtained from the patient to provide output information which identifies the presence or absence of an allelic variant, wherein the allelic variant is selected from the group consisting of: (i) rs6921438, (ii) rs4416670, (iii) rs6993770, and (iv) rs10738760, wherein if the nucleic acid sample is screened for the allelic variant rs6921438 and a guanine residue is detected at base 323 of SEQ ID No.1 at one or both alleles, a VEGF-based therapy is administered, wherein if the nucleic acid sample is screened for the allelic variant rs4416670 and a thymine residue is detected at base 221 of SEQ ID No. 2 at one or both alleles, a VEGF-based therapy is administered, wherein if the nucleic acid sample is screened for the allelic variant rs6993770 and a thymine residue is detected at base 235 of SEQ ID No. 3 at one or both alleles, a VEGF-based therapy is not administered, wherein if the nucleic acid sample is screened for the allelic variant rs10738760 and a guanine residue is detected at base 201 of SEQ ID No. 4 at one or both alleles, a VEGF-based therapy is administered.

Preferably, the VEGF-based therapy is an anti-VEGF drug, which may be selected from bevacizumab (Avastin™), ranibizumab (Lucentis™), lapatinib (Tykerb™), sunitinib (Sutent™), sorafenib (Nexavar™), axitinib, pazopanib and thiazolidinediones.

The sequences referenced herein have been deposited at the dbSNP database of the NCBI (www.ncbi.nlm.nih.gov/snp).

As used herein, an "allelic variation" refers to a variation in the nucleic acid and typically primary amino acid sequence of a gene in one or more alleles in a subject, such as a human patient. Allelic variations include single or multiple nucleic acid and amino acid substitutions, additions or deletions that have any one of a number of effect on protein expression, including without limitation: promoter activity that regulates transcription, frame-shift, early protein termination, protein mis-folding, altered protein processing, destruction (or enhancement) of active sites or binding sites of a protein, mis-splicing of an mRNA or any other property of a nucleic acid or protein that effects the expression and/or function of the final gene products.

A large number of methods, including high-throughput methods, are available for detection of SNPs and/or other allelic variations, for example, and without limitation, the PCR and Restriction Fragment Length Polymorphisms methods described in the Examples below. In one embodiment, DNA from a sample is sequenced (re-sequenced) by any method to identify a SNP or small allelic variation. A large variety of re-sequencing methods are known in the art, including high-throughput methods. Amplification-based methods also are available to identify allelic variations, such as SNPs, including, without limitation: PCR, reverse transcriptase PCR (RT-PCR), isothermic amplification, nucleic acid sequence based amplification (NASBA), 5' fluorescence nuclease assay (for example TAQMAN assay), molecular beacon assay and rolling-circle amplification. Other methods, such as Restriction Fragment Length Polymorphisms RFLP, also may be employed—as is appropriate and effective to identify variant allele(s). Assays may be multiplexed, meaning two or more reactions are carried out simultaneously in the same physical location, such as in the same tube or position on an array—so long as the reaction products of the multiplexed reactions can be distinguished. As a non-limiting example, TAQMAN or molecular beacon assays can be multiplexed by use of and by monitoring of accumulation or depletion of two different fluorochromes corresponding to two different sequence-specific probes. In most cases, the appropriate method is dictated by personal choice and experience, equipment and reagents on hand, the need for high-throughput and/or multiplexed methods, cost, accuracy of the method, and the skill level of technicians running the assay. Design and implementation of those techniques are broadly-known and are well within the abilities of those of average skill in the art.

In the implementation of the methods provided herein, and in particular in respect of the screening step, an array may be utilized. Arrays are particularly useful in implementing high-throughput assays. The array typically comprises one or more reagents, for example and without limitation, nucleic acid primers and/or probes, for identifying in a nucleic acid sample from a subject the occurrence of an allelic variation corresponding to one or more single nucleotide polymorphisms identified herein.

A sixth aspect of the present disclosure provides a solid support substrate having an array of affinity molecules deposited thereon, wherein the molecules have affinity for and/or hybridize to, one or more polynucleotides comprising single nucleotide polymorphisms identified herein as rs6921438, rs4416670, rs6993770, rs10738760, rs16873365, rs16873402, rs16873291, rs2375980, rs910611 and/or wherein the molecules have affinity for and/or hybridize to one or more of the genes selected from VLDLR, LRP12, ZFPM2 and KCNV2. The molecules are preferably polynucleotides, and are preferably the molecules are covalently attached to the substrate.

As used herein, the term "array" refers to reagents for facilitating identification of allelic variations in a gene located at two or more identifiable locations. In one embodiment, an array is an apparatus having two or more discrete, identifiable reaction chambers, such as, without limitation a 96-well dish, in which reactions comprising identified constituents are performed. In an exemplary embodiment, two or more nucleic acid primers or probes are immobilized onto a substrate in a spatially addressable manner so that each individual primer or probe is located at a different and (addressable) identifiable location on the substrate. Substrates include, without limitation, multi-well plates, silicon chips and beads. In one embodiment, the array comprises two or more sets of beads, with each bead set having an identifiable marker, such as a quantum dot or fluorescent tag, so that the beads are individually identifiable using, for example and without limitation, a flow cytometer. In one embodiment, in the context of the present disclosure, an array may be a multi-well plate containing two or more well reaction chambers with primers for amplifying DNA to identify SNPs or probes for binding specific sequences. As such, reagents, such as probes and primers may be bound or otherwise deposited onto or into specific locations on an array. Reagents may be in any suitable form, including, without limitation: in solution, dried, lyophilized or glassified. Useful array technologies include, for example and without limitation an Affymetrix GeneChip® Array, for example, GeneChip® CustomSeq® Resequencing Arrays (commercially available from Affymetrix Inc. of Santa Clara, Calif.) and like technologies. Informatics and/or statistical software or other computer-implemented processes for analyzing array data and/or identifying genetic risk factors from data obtained from a patient sample, are known in the art.

According to various methods of the present disclosure, the screening step produces an output signal which identifies the presence or absence of a specific allelic variant or gene expression level, or identifies an appropriate course of action. The course of action resulting from the signal output may, for example, be to administer or not administer a VEGF-based therapy. The output signal may take any appropriate form. It may, for example, be an audio or visual output signal, or may involve a light output, or a written communication.

The present disclosure is exemplified by reference to the following non-limiting examples. Example 1 describes the identification of the SNPs of the disclosure.

Example 1

Study Populations

1. The Framingham Heart Study (FHS)

The FHS, initiated in 1948, is a three-generation, community-based, prospective cohort study conducted in Framingham, Mass., USA. Serum VEGF levels were measured in third generation cohort participants (2002-2005) and genome-wide genotyping was performed on these individuals at Affymetrix (Santa Clara, Calif.) through an NHLBI funded SNP-Health Association Resource (SHARe) project. We chose not to include participants with cardiovascular disease, as the latter may influence VEGF levels. After excluding participants who had prevalent cardiovascular disease, which may influence their VEGF levels, or failed to meet quality control standards, 3,527 participants were enrolled.

2. The STANISLAS Family Study (SFS)

The SFS is a 10-year longitudinal survey involving 1,006 volunteer families from Vandoeuvre-lès-Nancy, France, whose members were free of chronic disease (cardiovascular or cancer) between 1993-1995. Plasma VEGF levels were measured at the second examination cycle (1998-2000) in a randomly selected sub-sample; of these 859 persons from 217 families, who also had DNA and met genotyping quality control criteria, were included.

3. Prospective Investigation of the Vasculature in Uppsala Seniors (PIVUS) Study The PIVUS study is a population-based study that enrolled 1,016 70-year old individuals living in the community of Uppsala, Sweden (2001-2004). Of these, 999 persons provided DNA for genetic studies and after exclusions for prevalent cardiovascular disease and inadequate genotyping quality, 868 participants were eligible. Characteristics of the 5,273 study participants are presented in Table 1.

TABLE 1

| Characteristics | FHS | SFS[†] | PIVUS Study |
|---|---|---|---|
| Number of participants | 3,527 | 859 | 868 |
| Mean circulating VEGF level (ng/L), median (IQR) * | 280 (294.7) | 27.4 (28.2) | 187.5 (210.6) |
| Mean age (SD) at VEGF measurement, mean (SD) | 40.0 (8.7) | 29.83 (14.5) | 70.2 (0.2) |
| Women (%) | 1890 (53.2) | 428 (49.8) | 454 (52.3) |
| Cardiovascular risk factor at VEGF measurement | | | |
| Systolic blood pressure, mean (SD) | 116.7 (14.0) | 120.3 (12.8) | 149.6 (22.7) |
| Hypertension (%) | 561 (15.9) | 23 (2.7) | 606 (69.8) |
| Diabetes mellitus (%) | 89 (2.5) | 0 | 68 (7.8) |
| Current smoker (%) | 544 (15.3) | 188 (21.9) | 93 (10.7) |
| Central obesity (%) | 1315 (37.2) | 37 (44.3) | 266 (30.6) |
| Metabolic syndrome (%) | 693 (19.6) | 19 (2.2) | 198 (22.8) |

IQR: Inter-Quartile Range; SD: Standard Deviation;
* Serum levels for the FHS and the PIVUS study, and plasma levels for the SFS;
[†]by design, SFS participants were free of chronic disorders (cardiovascular or cancer) and had no personal history of cardiovascular disease at the time of inclusion (VEGF levels and covariates for the present analysis were measured during the second examination cycle in 1998-2000); all individuals with CVD (cardiovascular disease), defined in the FHS as presence of stroke, congestive heart failure, coronary heart disease or intermittent claudication, were excluded before analyses in FHS and PIVUS.

Laboratory Measurements of VEGF Levels

VEGF levels were measured in serum for the FHS and PIVUS and plasma for the SFS. In all 3 studies venous blood samples were drawn after an overnight fast, immediately centrifuged and stored appropriately (at −80° C. in FHS and PIVUS and at −196° C. in liquid nitrogen in SFS) until VEGF measurements were undertaken. At FHS, serum VEGF was measured using a commercial ELISA assay (R&D Inc.). In SFS and PIVUS plasma VEGF and serum VEGF quantification respectively was performed by Randox Ltd (Crumlin, UK), using a biochip array analyzer (Evidence®). In all studies both diffusible VEGF isoforms ($VEGF_{121}$ and $VEGF_{165}$) were detected.

The average inter-assay coefficients of variation were 2.1% for serum VEGF in the FHS, less than 9% in the SFS and less than 15% in the PIVUS study.

Since serum VEGF had been measured in the FHS and PIVUS and plasma for VEGF in the SFS, we checked the correlation between the 2 types of specimens. VEGF was measured in a subset (n=18) of matched plasma and serum samples from the SFS. Plasma VEGF was lower (42±28 ng/L, mean±SD) than serum VEGF (361±223 ng/L); There was a strong correlation between plasma and serum VEGF (r=0.76, p=0.0002) which strengthens our study.

Genotyping

1. FHS

Genome-wide genotyping in the FHS was performed on the Affymetrix GeneChip Human Mapping 500K Array Set® and 50K Human Gene Focused Panel®. The set of genotyped input SNPs used for imputation was selected based on their highest quality GWA data. From a total of 534,982 genotyped autosomal SNPs in FHS, we used 378,163 SNPs in the imputation after filtering out 15,586 SNPs for Hardy-Weinberg disequilibrium ($p<1\times10^{-6}$), 64,511 SNPs for missingness>0.03, 45,361 SNPs for a test of differential missingness yielding a $p<1\times10^{-9}$ (mishap test in PLINK, http://pngu.mgh.harvard.edu/purcell/plink/), 4,857 SNPs for >100 Mendel errors, 67,269 SNPs for a minor allele frequency<0.01, 2 SNPs due to strandedness issues upon merging data with HapMap, and a further 13,394 SNPs because they were not present on HapMap. We used the Markov Chain Haplotyping (MaCH) package (http://www.sph.umich.edu/csg/abecasis/MACH, version 1.0.15 software) and imputed to the plus strand of NCBI build 36, HapMap release #22. For each imputed SNP, imputation quality was estimated as the ratio of the empirically observed dosage variance to the expected binomial dosage variance. After quality control and filtering, FHS had either genotyped or imputed data for 2,540,223 autosomal SNPs. From a total of 10,886 genotyped SNPs on the X chromosome, we used 7,795 SNPs in the imputation after filtering out 3,091 SNPs for Hardy-Weinberg $p<1\times10^{-6}$ (n=159), missingness>0.03 (n=450), minor allele frequency<0.01 (n=1851), male heterozygote count>45 (n=12), and a further 619 SNPs because they were not present on HapMap. We used the IMPUTE package (https://mathgen.stats.ox.ac.uk/impute/impute.html, version 0.5.0) and imputed to the plus strand of NCBI Build 35, Hapmap release #21.

2. SFS

The SNPs were genotyped by Genoscreen© (http://genoscreen.fr) using a Sequenom® iPLEX Gold assay—Medium Throughput Genotyping Technology.

3. PIVUS Study

The SNPs were genotyped as part of a 96-plex assay at the SNP technology platform in Uppsala University (http://www.genotyping.se/) using the Illumina BeadXpress system from Illumina Inc. Genotyping calls were done with Illumina BeadStudio software.

Statistics

VEGF levels were natural log-transformed to normalize their distribution.

Genome-Wide Association Analysis in the FHS

A linear mixed effects model accounting for familial relatedness was used to evaluate the association of each SNP with VEGF levels. An additive genetic model with one degree of freedom was used. In a first step (Model A), analyses were adjusted for age, sex, and the ninth principal component.

In a second step designed to explore potential mechanisms, we additionally adjusted our most significant associations for covariates previously found to be associated with serum VEGF levels: compared to Model A, Model B was additionally adjusted for hypertension; model C for smoking; model D for central obesity and model E for the presence of a metabolic syndrome.

Genetic Association Study in the SFS and the PIVUS Study

In order to confirm our findings in the FHS, we genotyped 25 SNPs in two independent samples. To select a parsimonious number of SNPs for replication we used criteria of strength of association (p-value), whether the SNP was genotyped or imputed, linkage disequilibrium (LD) between SNPs and functionality.

From all SNPs associated with VEGF levels at a p-value<$5 \times 10^{-8}$ in the discovery cohort, we excluded SNPs with minor allele frequencies (MAF)<0.05 as well as those imputed SNPs with low imputation quality (ratio of the empirically observed dosage variance to the expected binomial dosage variance<0.6). The remaining SNPs were grouped by "bins", each bin comprising SNPs that are in very strong linkage disequilibrium (LD) with each other, i.e. with an $r^2$>0.8 with the most significant SNP in the bin. Within each bin we selected one SNP for replication (except for the bin with the most significant associations where 2 SNPs were selected). Typically, we selected the SNP with the lowest p-value within each bin. In 6 bins a SNP with a slightly higher p-value was chosen either because this SNP had been directly genotyped in the discovery cohort, whereas the SNP with the lowest p-value in the bin had been imputed (rs1776721 and rs1886979) or because there were stronger arguments for functionality for the SNP with the slightly higher p-value (rs16873291, rs1349319, rs6475920 and rs10967492). A linear regression model using the same covariates and analytic strategy as in the FHS was implemented.

Joint Analysis of the FHS, SFS and PIVUS Study

For SNPs that were successfully genotyped in the SFS and the PIVUS study we performed a meta-analysis of the SNP-phenotype associations, using a fixed effects inverse-variance meta-analysis technique for the combination of results from the FHS and the PIVUS study (which had both measured VEGF levels in the serum) and an effective sample size weighted meta-analysis for the combination of results from all three studies, to account for the different scales of VEGF levels in serum and plasma.

Genetic Score

The methods used for computing a genetic score are detailed below. The phenotype variance explained by this genetic score was separately calculated in the FHS, the SFS and the PIVUS study, using regression models that included age and sex as covariates.

Step 1:

We selected SNPs with independent effects by running a conditional GWAS. This was done in a forward stepwise fashion. First we ran a GWAS adjusting for age, gender, the ninth principal component and the most significantly associated SNP (rs6921438). We then ran a GWAS additionally adjusting for the most significantly associated SNP in the aforementioned conditional GWAS. This process was repeated, by adding the most significantly associated SNP as a new covariate to the regression model, until all SNPs independently associated with VEGF level at a p-value<$5 \times 10^{-8}$ were selected. All selected independent SNPs with a minor allele frequency>5% were used to compute the genetic score (see Table 2). In the PIVUS study, as rs6921438 genotypes were not available, rs4513773 was used instead to compute the genetic score ($r^2$ with rs6921438=0.90)

Step 2:

Genotypes for the SNPs selected in step 1 were coded as 0, 1 or 2 for genotyped SNPs (according to the number of minor alleles) and the imputed allele dosage was used for imputed SNPs.

To compute the genetic score the genotype value was weighted by the effect size estimate from the GWAS (see Table 2):

Risk Score=SNP1_estimate*SNP1_genotype+
SNP2_estimate*SNP2_genotype+
SNP3_estimate*SNP3_genotype+
SNP4_estimate*SNP4_genotype Step 3:

We estimated the proportion of phenotype variance explained by each SNP incorporated in the risk score ($h^2_q$; see Table 2); $h^2_q$ was computed as follows, using the GWAF R-package:

$$h_q^2 = \max\left(0, \frac{\sigma_{G.null}^2 + \sigma_{e.null}^2 - \sigma_{G.full}^2 - \sigma_{e.full}^2}{\text{Var}(y)}\right)$$

wherein:

Var(y)=total phenotypic variance;

$\sigma^2_{G.null}$ and $\sigma^2_{e.null}$=the polygenic variance and error variance when modeling without the tested SNP; and $\sigma^2_{G.full}$ and $\sigma^2_{e.full}$=the polygenic variance and error variance when modeling with the tested SNP.

VEGF Gene Expression Analysis in Peripheral Blood Mononuclear Cells (PBMCs)

Sample preparation and quantification of the PBMC messenger RNA (mRNA) of VEGF spliced forms. Two-hundred and twenty samples from the SFS were randomly selected for inclusion in the PBMCs transcriptomic study. Fresh whole blood (10 mL) was collected by standardized venipuncture in EDTA tubes (Vacutainer™; Becton Dickinson, NJ, USA). PBMCs were isolated by centrifugation on a density gradient of Ficoll (Ficoll-Paque™ PLUS; Amersham BioSciences) and stored at −80° C. until RNA extraction according to a well-validated protocol, with high recovery of lymphocyte (97.5%). Total RNA was subsequently extracted with the MagNaPure automate, using the MagNA Pure LC RNA HP isolation kit and RNA HP Blood External lysis protocol (Roche Diagnostics, France). Reverse transcription of total RNA was performed using 200 units of M-MuLV Reverse Transcriptase with 0.25 µg of oligos(dt) (Promega, France) according to a previous described protocol. Quantification of the transcripts coding for the $VEGF_{121}$ and $VEGF_{165}$ isoforms, and the beta 2 microglobulin (B2M) control gene, was performed using Taq-Man® and LightCycler technologies (LC TaqMan Master kitRoche Diagnostics, France). All experiments were performed in duplicate. The detection level for each transcript was between 1 and 10 copies for both transcripts and for B2M. RT-PCR optimization and specificity of RT-PCR products were examined using SYBR® Green technology (LC FastStart DNA Master$^{PLUS}$ SYBR Green I kit, Roche Diagnostic, France), melting curves analysis and agarose gel electrophoresis of the PCR amplicons. Primers and probes were designed to specifically amplify the spliced forms of VEGF based on their splicing sites with specific reverse primers or hydrolyzation probes spanning the variant specific exon boundaries, which also avoids amplification of contaminating genomic DNA. Hydrolyzation probes were labeled with the reporter dye FAM (6-carboxy-fluorescein phosphoramidite) at the 5' end and the quencher dye TAMRA (5-carboxyl-tetramethyl-rhodamine) at the 3' end.

For all assays, intra- and inter-run variability were 11% and 5% respectively. PCR products for each VEGF mRNA spliced variant amplification were purified with a PCR purification kit (QiaQuick, Qiagen, France). The product concentrations were measured in a spectrophotometer, the molecule concentrations were calculated, and a standard curve was generated for each transcript using serial dilutions of products ranging from 1 or 10 to $10^7$ molecules/µL. The copy number of unknown samples was calculated by setting their PCR cycle number (Crossing Point: CP) to the standard curve and normalized to the housekeeping B2M gene. Results are presented as copies of the target gene product per $10^6$ copies of B2M. Primer efficiencies were calculated according to the equation E=10[−1/slope]. All investigated transcripts had real-time PCR efficiency rates above 1.9.

PBMCs VEGF Protein Measurements

PBMC VEGF (121 and 165) protein quantification was performed by Randox Ltd (Crumlin, UK), with a biochip array analyzer (Evidence®) using a high sensitivity kit as previously described.[7] PBMC VEGF concentrations were log 10-transformed in all analyses in order to improve normality, were adjusted for the effect of between-run variation and regressed on mean values of all samples measured in each run. Grubbs' test was applied for detection of the extreme values in the data (log transformed VEGF) and there were no outliers at the 5% level. The average inter-assay coefficient of variation was 5.7%.

Statistical Analysis

A linear mixed effects model that accounts for within family correlation was used to evaluate the association of each of the SNPs successfully genotyped in the SFS with each of the two transcript levels ($VEGF_{121}$ and $VEGF_{165}$) and with natural log-transformed PBMC VEGF concentration, assuming an additive genetic model. These analyses were adjusted for age and sex.

Biological Pathway Analysis

Genes located close to associated SNPs were investigated for relevant networks by the Ingenuity Pathway Analysis (IPA) software (Ingenuity Systems, www.ingenuity.com). To build networks, IPA queries the Ingenuity Pathways Knowledge Base for biological interactions between identified "focus genes", in this case genes close to SNPs significantly associated with circulating VEGF levels in the GWAS, and all other gene objects stored in the knowledge base. It then generates a set of networks with a maximum network size of 35 genes. An underlying assumption is that highly-interconnected networks are likely to represent significant biological function, thus IPA optimizes for triangular relationships between genes, favoring denser networks over more sparsely connected ones. Networks are displayed graphically as "nodes" (corresponding to genes or gene products) and the biological relationships between the nodes, referred to as "edges". IPA also computes a score, representing the $-\log_{10}$ (p-value), where the p-value is the probability of finding f or more focus genes in a set of n genes randomly selected. If there are 'n' genes in the network and f of them are focus genes, the p-value is the probability of finding T or more focus genes in a set of 'n' genes randomly selected from the Global Molecular Network. It is calculated using Fisher's exact test.

GWAS of VEGF Levels in the FHS

Figure 2:
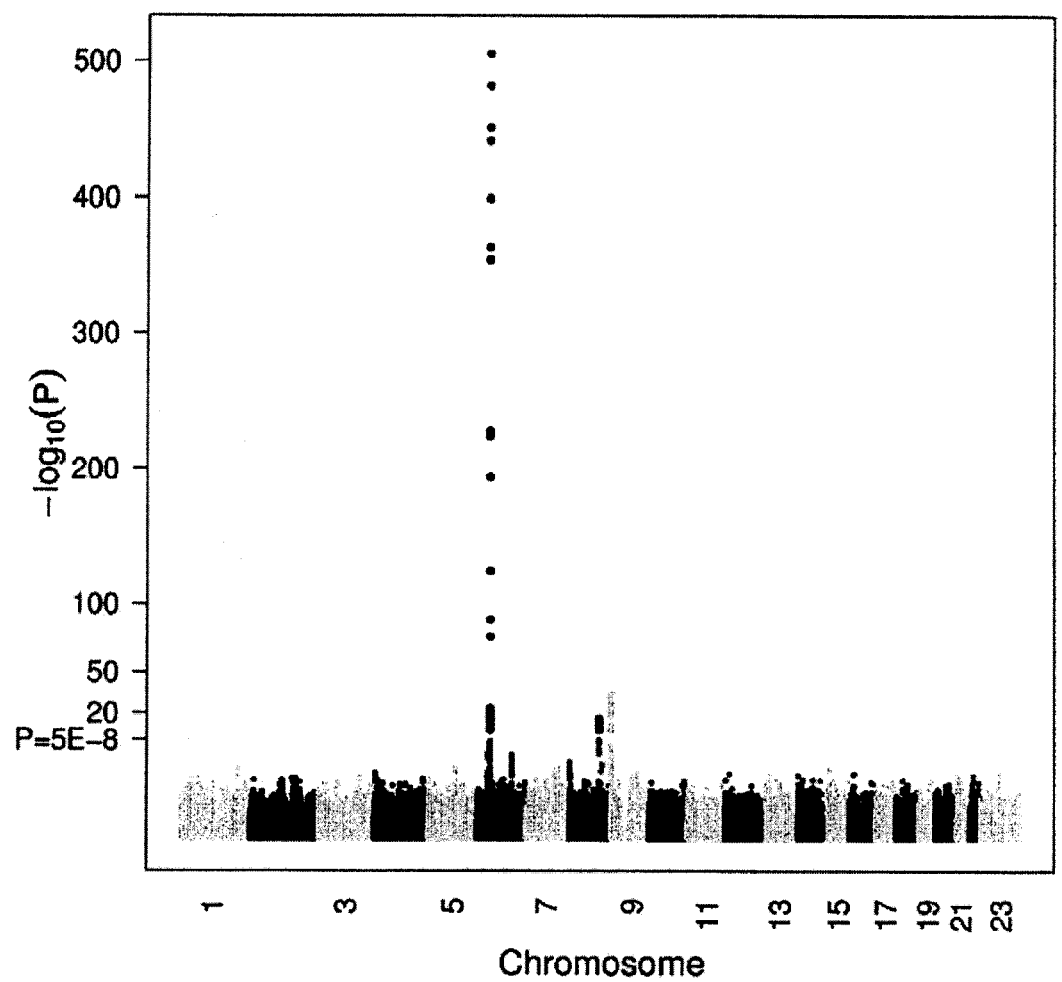
FIG. 2 is a Manhattan plot showing individual p-values against their genomic position for GWAS of serum VEGF levels. Within each chromosome (x-axis), results are plotted left to right from p-terminal end. Dashed line indicates preset threshold for genome-wide significance, $p=5.0\times10^{-8}$; solid line threshold for suggestive associations, $p=4.0\times10^{-7}$.

The quantile-quantile (QQ) plot showed an excess of extreme p-values but no evidence of systematic inflation of the genomic control inflation factor (λ=1.02) (see FIG. 1). The genome-wide plot of p-values for the individual SNPs against their genomic position is shown in FIG. 2. A total of 140 SNPs cleared the threshold for genome-wide significance at $5\times10^{-8}$. These are shown in FIGS. 6A-6E.

The 140 SNPs that cleared the threshold for genome-wide significance were located in three chromosomal regions: 6p21.1, 8q23.1, 9p24.2. These are shown in FIG. 7.

Figure 3A:
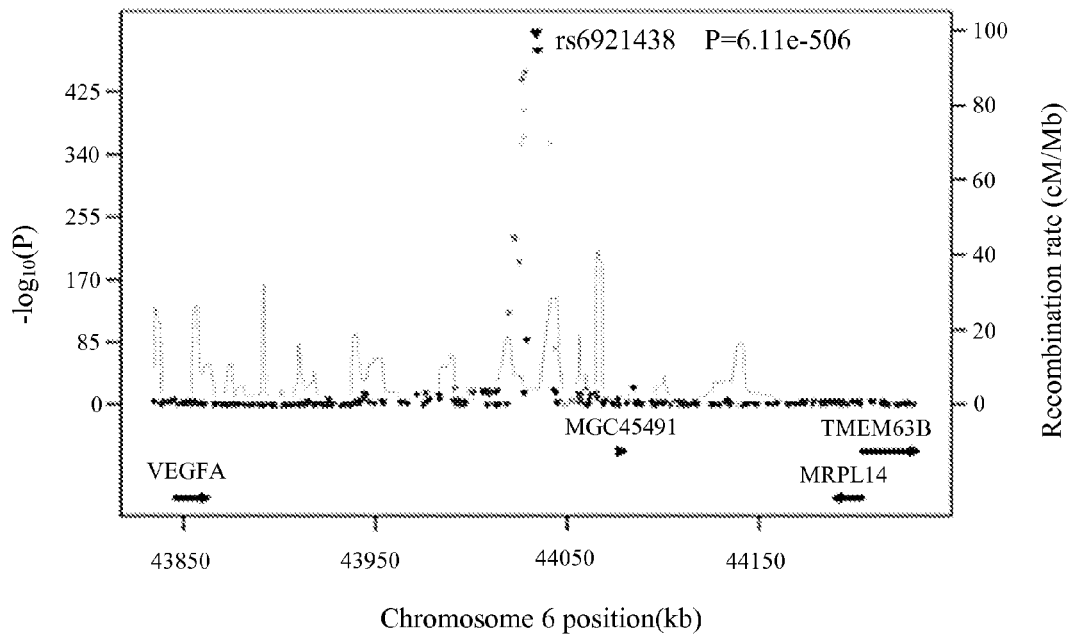
FIGS. 3A-3C show regional plots for associations in region centered on rs6921438 (FIG. 3A), rs6993770 (FIG. 3B) and rs10738760 (FIG. 3C).
Figure 3B:
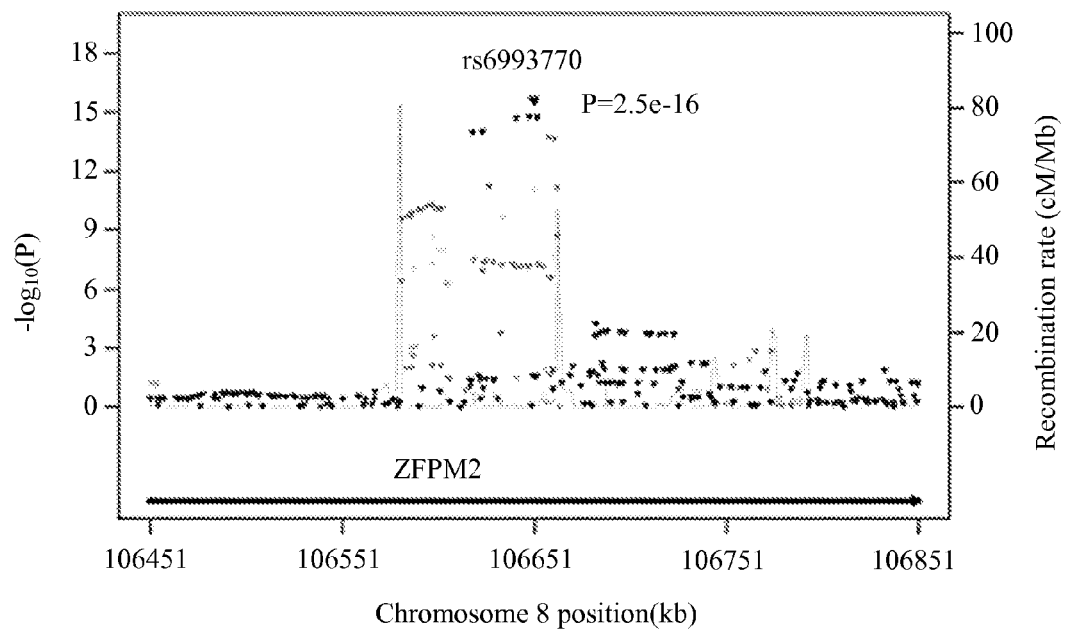
Figure 3C:
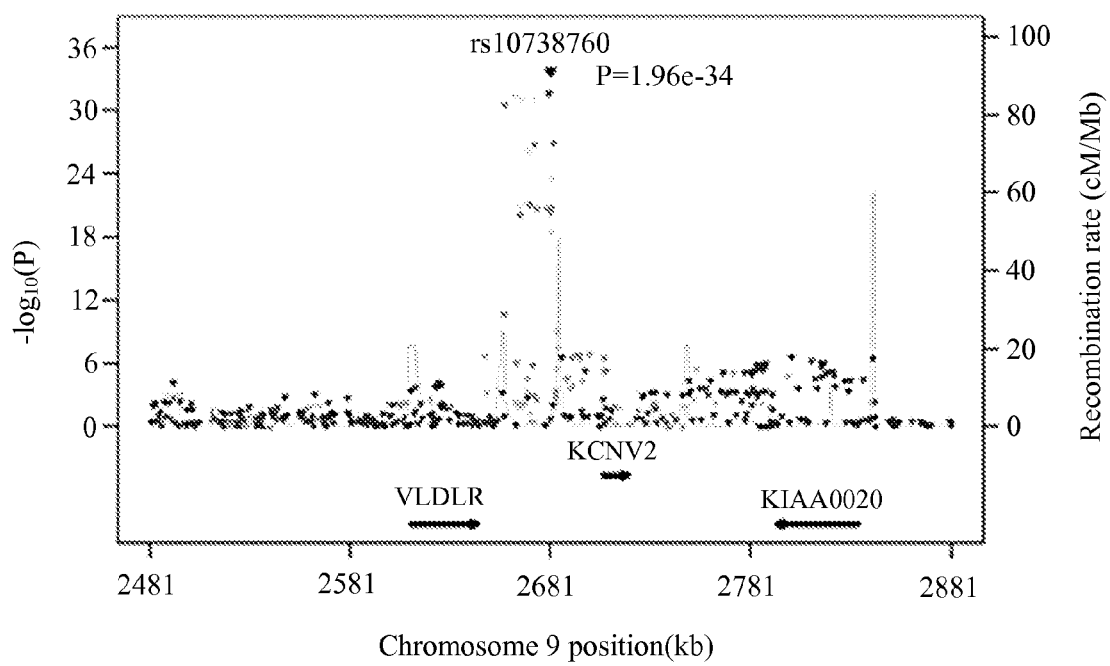

The most significant association was found with rs6921438 on chromosome 6p21.1 ($p=6.11\times10^{-506}$), at 171 kb downstream of the VEGF gene, and close to the mitochondrial ribosomal protein L14 gene (MRPL14) and the MCG45491 gene (C6orf223), encoding an uncharacterized protein. Sixty-seven other SNPs on chromosome 6p21.1 were also associated with VEGF levels at $p<5\times10^{-8}$ (see FIG. 3A). When running a conditional GWAS adjusting for rs6921438, one other SNP in 6p21.1 (rs4416670) still yielded a genome-wide significant association, suggesting that two variants in this region independently modulate VEGF levels. In the 8q23.1 region the SNP yielding the most significant association with VEGF levels (rs6993770, $p=2.50\times10^{-16}$) is located in the zinc finger protein, multitype 2 (ZFPM2) gene and 980.4 kb away from the low-density lipoprotein receptor-related protein 12 gene (LRP12). Forty-three SNPs in LD with rs6993770 were also associated with VEGF levels at $p<5\times10^{-8}$ (see FIG. 3B). A conditional GWAS adjusting for rs6993770, rs6921438 and rs4416670 did not yield any other genome-wide significant association in chromosome 8q23.1. The most significant association on 9p24.2 was observed with rs10738760 ($p=1.96\times10^{-34}$), located close to the very low density lipoprotein receptor (VLDLR) and potassium voltage-gated channel subfamily V, member 2 (KCNV2) genes. Twenty-nine SNPs in LD with rs10738760 were also associated with VEGF levels at $p<5\times10^{-8}$ (FIG. 3C). None reached genome-wide significance in a conditional GWAS adjusted for rs6921438, rs4416670, rs6993770 and rs10738760.

A genetic score including the four SNPs yielding genome-wide significant associations with VEGF levels in the conditional GWAS was computed. Results of the main and conditional GWAS within the Framingham Heart Study sample for the SNPs retained in the genetic score calculation are shown in Table 2. This score explained 47.6% of serum VEGF variability ($p=2.19\times10^{-644}$).

Figure 4:
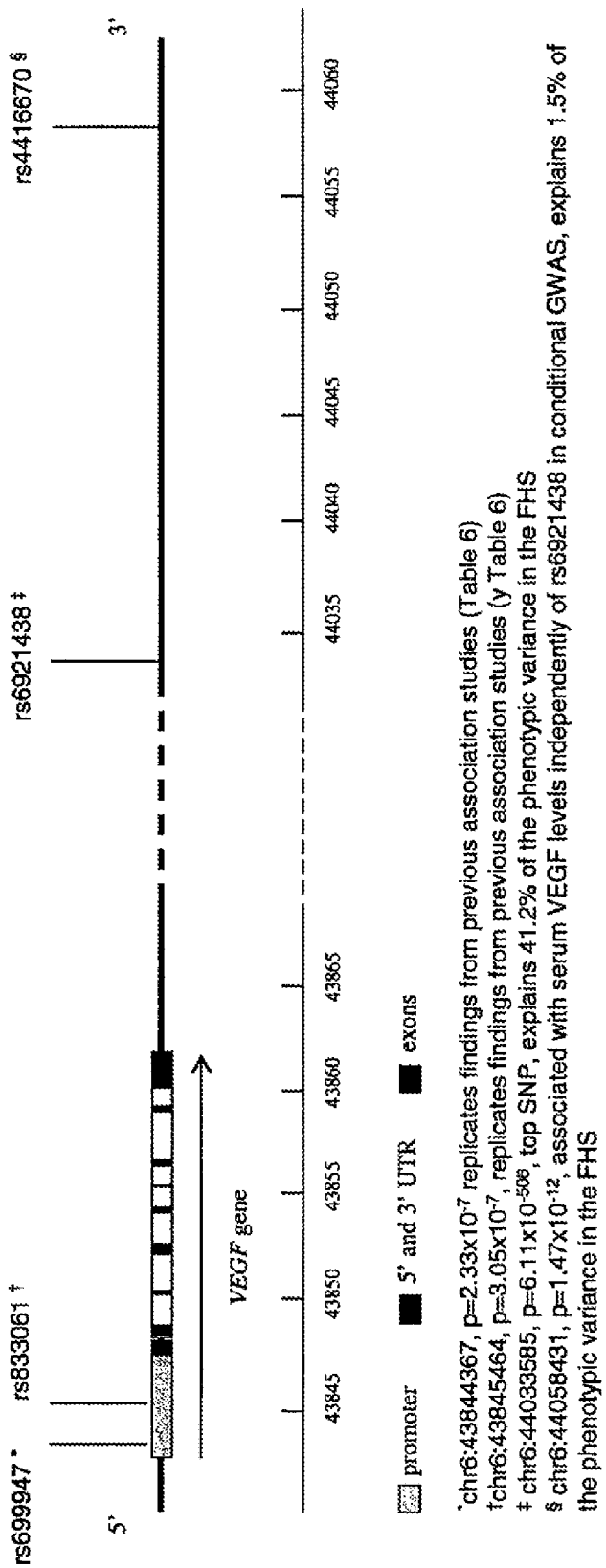
FIG. 4 shows the genomic organization of the VEGF gene and localization of the SNPs identified in the genetic association and transcriptomic studies.

The genetic score for a single SNP, rs6921438, explains 41.2% of the phenotypic variation in FHS (see FIG. 4).

TABLE 2

| SNP | chr | position | CA | CAF | Estimate in main GWAS* | SE in main GWAS* | p in main GWAS* | p in conditional GWAS† | $h^2_q$ % |
|---|---|---|---|---|---|---|---|---|---|
| rs6921438 | 6 | 44033585 | G | 0.51 | 0.7199 | 0.0149 | $<5\times10^{-324}$ | $<5\times10^{-324}$ | 41.19 |
| rs10738760 | 9 | 2681186 | A | 0.49 | 0.2812 | 0.0230 | $1.96\times10^{-34}$ | $3.78\times10^{-47}$ | 4.97 |

TABLE 2-continued

| SNP | chr | position | CA | CAF | Estimate in main GWAS* | SE in main GWAS* | p in main GWAS* | p in conditional GWAS† | $h^2_q$ % |
|---|---|---|---|---|---|---|---|---|---|
| rs6993770 | 8 | 106650704 | T | 0.32 | −0.1667 | 0.0203 | $2.50 \times 10^{-16}$ | $5.45 \times 10^{-30}$ | 2.03 |
| rs4416670 | 6 | 44058431 | T | 0.55 | 0.1342 | 0.0190 | $1.47 \times 10^{-12}$ | $4.79 \times 10^{-9}$ | 1.46 |

CA: coded allele
CAF: coded allele frequency;
Chr: chromosome;
GWAS: genome-wide association study;
$h^2_q$: percentage of phenotypic variance explained;
SE: standard error;
*adjusted for age, sex, and the ninth principal component;
†with all four SNPs in the same model, additionally adjusted for age, sex, and the ninth principal component.

Replication Studies

We sought to replicate our most significant results in two independent cohorts. Of the 25 SNPs selected for replication, 24 were successfully genotyped in the SFS and 20 in the PIVUS study, as shown in FIG. 7. Of these, 17 and 20 respectively reached nominal significance in association with VEGF levels, with the same direction of effect (FIG. 7). When meta-analyzing the results of the FHS and the PIVUS study, which both used serum VEGF levels, for the 19 SNPs genotyped in both studies, all 19 SNPs were associated with VEGF levels at p<0.05 (FIG. 7). The joint meta-analysis of results from all three studies, using an effective sample size weighted meta-analysis, is displayed in FIG. 7. There was statistically significant heterogeneity between studies for a few but not all SNPs in each locus, due to differences in effect size, but not in direction of effects. Table 3 shows the test of heterogeneity between studies in the meta-analyses combining discovery and replication cohorts. The genetic score explained 16.6% (p=$1.75 \times 10^{-36}$) of observed plasma VEGF variability in the SFS and 48.4% (p=$3.31 \times 10^{-180}$) of observed serum VEGF variability in the PIVUS study.

The observed associations remained unchanged in each of the three cohorts after adjusting for hypertension, current smoking, central obesity and metabolic syndrome. Table 4 shows the secondary genetic association analysis adjusting for clinical covariates previously found to be associated with VEGF levels. All analyses were adjusted for age, sex, and principal components. Model B was additionally adjusted for hypertension; model C for smoking; model D for central obesity; model E for the presence of a metabolic syndrome.

VEGF Gene Expression Analysis

In order to better characterize the functional role of the SNPs identified in the GWAS we quantified mRNA expression of the two splice variants corresponding to the diffusible isoforms of VEGF, $VEGF_{121}$ and $VEGF_{165}$, in PBMCs of 220 SFS participants. The association of VEGF mRNA levels with the 24 SNPs successfully genotyped in the SFS was assessed.

At the nominal significance level, 1 SNP on chromosome 6p21.1, 4 SNPs on chromosome 8q23.1 and 1 SNP on chromosome 9p24.2 were associated with $VEGF_{121}$ mRNA levels (see Table 5).

TABLE 5

| Phenotype | SNP | Chr | position | CA | CAF | beta† | SE | p | $h^2_q$ % |
|---|---|---|---|---|---|---|---|---|---|
| mRNA_121 | rs16873365 | 8 | 106627411 | T | 0.22 | 22.71 | 7.22 | 0.002 | 4.73 |
| mRNA_121 | rs16873402 | 8 | 106658423 | T | 0.33 | 12.15 | 5.10 | 0.017 | 2.84 |
| mRNA_121 | rs6993770 | 8 | 106650704 | T | 0.32 | 12.06 | 5.23 | 0.021 | 2.82 |
| mRNA_121 | rs16873291 | 8 | 106597206 | T | 0.31 | 11.95 | 5.37 | 0.026 | 2.47 |
| mRNA_121 | rs2375980 | 9 | 2682622 | G | 0.42 | 10.15 | 4.75 | 0.032 | 2.03 |
| mRNA_121 | rs910611 | 6 | 44058829 | C | 0.08 | −19.47 | 9.49 | 0.040 | 2.13 |

Figure 5:
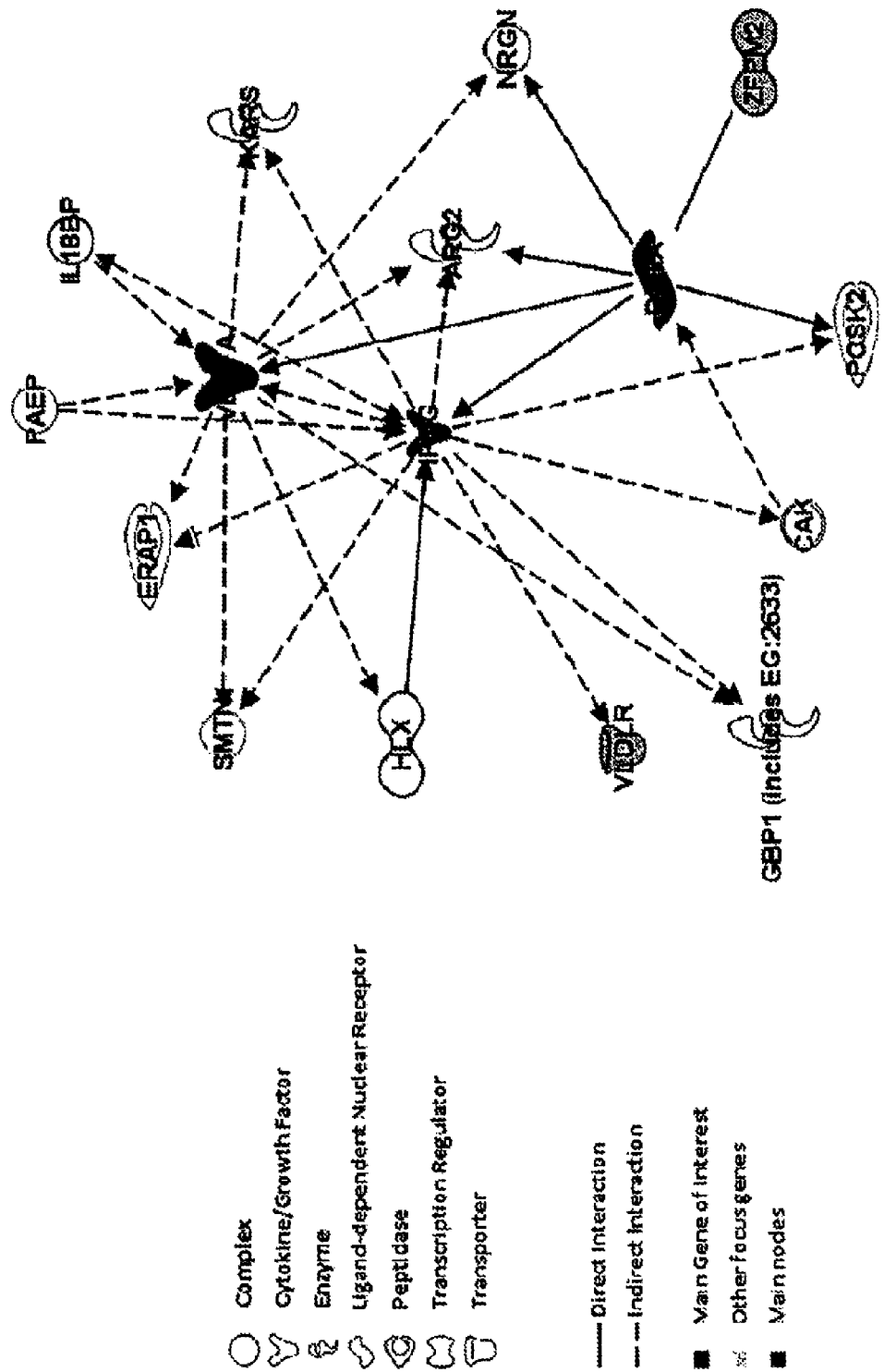
FIG. 5 shows a Putative Gene Network based on Ingenuity Path Analysis. Edges are displayed with labels describing the nature of the relationship between the nodes. Lines between genes represent known interactions and the nodes are displayed using various shapes which represent the functional class of the gene product (legend).

*log-transformed;
†effect estimate for the minor allele;
CAF: Coded Allele Frequency;
Chr: chromosome;
$h^2_q$: variance explained;
SE: standard error Biological Pathway Analysis Using the Ingenuity Pathway Analysis software (IPA, Ingenuity Systems, www.ingenuity.com) we explored functional relationships between VEGF and the genes closest to the SNPs on chromosome 8q23.1 and 9p24.2 that were significantly associated with circulating VEGF levels. In each case we selected the genes closest to the identified SNPs, as in FIG. 7, to identify plausible biological pathways. We selected five focus genes: VEGF; ZFPM2; LRP12; VLDLR; and KCNV2. The IPA network analysis identified relationships among three of these five focus genes (VEGF, ZFPM2 and VLDLR) as part of a larger network of 35 genes. The probability of finding 3 or more focus genes in a set of 35 genes randomly selected from the Global Molecular Network was p=$10^{-8}$, suggesting that the presence of three of our five focus genes in this network was unlikely to occur by chance. FIG. 5 shows a subset of this network, including only interactions between VEGF and the two other focus genes in the network, with 2 or fewer intermediate nodes.

Principal Findings

In this first GWAS of circulating VEGF levels undertaken in 3,527 community individuals of European descent, we identified novel genetic associations: 140 SNPs reached genome-wide significance. Of these, 4 SNPs were independently associated with VEGF levels (rs6921438 and rs4416670 on chromosome 6p21.1, rs6993770 on chromosome 8q23.1 and rs10738760 on chromosome 9p24.2). We found evidence of replication for selected SNPs in 1,727 individuals of European descent from two independent community-based samples. The SNPs are located close to the VEGF and MRPL14 genes (chromosome 6p21.1), within the ZFPM2 gene (chromosome 8q23.1), and between the VLDLR and KCNV2 genes (chromosome 9p24.2). In a subset of participants we found that 6 of 25 selected SNPs yielding genome-wide significant associations with circulating VEGF levels were also associated with VEGF mRNA levels ($VEGF_{121}$ splice variant) in PBMCs.

Using a hypothesis-free genome-wide approach, the present study revealed novel associations with 140 SNPs. Of these, 68 SNPs are located on chromosome 6 approximately 150 kb downstream from the 3' end of the VEGF gene, far from previously tested candidate SNPs. None of the SNPs that reached genome-wide significance in our analysis, on chromosome 6p21.1, 8q23.1 and 9p24.2, had been examined previously in relation with circulating VEGF levels.

The data support that six of the SNPs associated with circulating VEGF levels in our GWAS also modulate the expression of the VEGF splice variant in PBMCs of community-based persons. The diffusible VEGF isoforms, VEGF and VEGF, are released by a variety of tumor and normal cells, including PBMCs. VEGF lacks a heparin-binding domain and has a higher migration but lower mitogenic potency than VEGF.

Potential Mechanisms Mediating Observed Genetic Associations

The data demonstrate that almost half the inherited component of circulating VEGF levels is explained by genetic variants located downstream from the VEGF gene on chromosome 6p21.1. The conditional GWAS demonstrates that this region may harbor at least two distinct loci that are independently associated with circulating VEGF levels. Although located relatively far from the VEGF gene, results from our transcriptomic analysis indicate that this region could indeed contain functional variants modulating VEGF gene expression.

Genome-wide significant associations with circulating VEGF levels were also identified for SNPs located on chromosome 8q23.1 and 9p24.2. Although these trans-effects explain a much smaller proportion of the heritability of VEGF levels, they provide important clues about the pathways involved in the regulation of VEGF expression. The SNPs on chromosome 8q23.1 are located in introns 4 and 5 of the ZFPM2 gene. This gene encodes a widely expressed member of the Friend of GATA family of transcription factors that modulate the activity of the GATA family proteins, which are important regulators of embryogenesis and also seem to play a significant role in endothelial cell biology. The second closest gene to the SNPs identified on chromosome 8q23.1 is LRP12, encoding a low-density lipoprotein receptor-related protein that interacts with proteins related to signal transduction pathways and is differentially expressed in many cancer cells. The SNPs on chromosome 9p24.2 are located between the VLDLR and KCNV2 genes. VLDLR encodes a lipoprotein receptor involved in the metabolism of apolipoprotein-E-containing triacylglycerol-rich lipoproteins. Like VEGF, VLDLR appears to modify the risk of developing age-related macular degeneration, and data show that VLDLR could play a central role in a network of interacting angiogenic genes activated in response to hypoxia. KCNV2 encodes a member of the potassium voltage-gated channel subfamily V involved in regulation of neurotransmitter release, neuronal excitability and heart rate. The in silico biological pathway analysis suggests that ZFPM2 and VLDLR are candidate genes that underlie the observed SNP associations with circulating VEGF levels. Further research may explore the mechanisms underlying the associations of cis- and trans-acting genetic variants with circulating VEGF levels, such as modulation of gene expression, differential splicing or mRNA degradation.

The findings from this first GWAS of circulating VEGF levels emphasize the importance of screening for genetic variation modulating biomarker levels not only within and in close proximity to the gene encoding the protein under investigation, but also in more distant potentially regulatory regions, including on other chromosomes. The strength of the observed associations and the fact that we were able to replicate our findings in two independent cohorts support these associations. This is further supported by the association of several of these genetic variants with VEGF gene expression in PBMCs.

TABLE 3

| | | $P_{heterogeneity}$ | |
|---|---|---|---|
| SNP | Chr | Inverse variance weighted meta-analysis (FHS + PIVUS) | Effective sample size weighted meta-analysis (FHS + SFS + PIVUS) |
| rs6921438 | 6 | 1 | $5.50 \times 10^{-21}$ |
| rs4513773 | 6 | 0.52 | 0.19 |
| rs9472159 | 6 | $5.70 \times 10^{-3}$ | $6.07 \times 10^{-18}$ |
| rs9369434 | 6 | $4.32 \times 10^{-15}$ | $7.74 \times 10^{-26}$ |
| rs1776717 | 6 | 0.18 | 0.69 |
| rs1776721 | 6 | 0.31 | 0.068 |
| rs1886979 | 6 | 0.90 | 0.20 |
| rs9472155 | 6 | 0.20 | 0.056 |
| rs844294 | 6 | 0.71 | 0.14 |
| rs4416670 | 6 | 0.10 | 0.23 |
| rs910611 | 6 | 0.52 | 0.13 |
| rs6993770 | 8 | 0.087 | 0.099 |
| rs16873402 | 8 | 0.033 | 0.011 |
| rs16873365 | 8 | 0.052 | 0.022 |
| rs7013321 | 8 | 1 | 0.41 |
| rs6993696 | 8 | 0.67 | 0.39 |
| rs16873291 | 8 | 0.069 | 0.098 |
| rs1349319 | 8 | 0.66 | 0.70 |
| rs10738760 | 9 | 0.14 | $2.20 \times 10^{-3}$ |
| rs6475920 | 9 | 0.78 | $7.20 \times 10^{-3}$ |
| rs4741756 | 9 | 0.11 | $9.84 \times 10^{-4}$ |
| rs2375980 | 9 | 0.44 | 0.018 |
| rs10122587 | 9 | 1 | 0.015 |
| rs10967492 | 9 | 1 | $5.79 \times 10^{-3}$ |
| rs10967470 | 9 | 1 | 0.016 |

TABLE 4

| SNPID | Chr | Position | p (FHS) | p (PIVUS) | p (SFS) | Meta-p (FHS + PIVUS)* | Meta-p (all)† |
|---|---|---|---|---|---|---|---|
| Model B | | | | | | | |
| rs6921438 | 6 | 44033585 | $1.72 \times 10^{-506}$ | NA | $1.84 \times 10^{-39}$ | $1.72 \times 10^{-506}$ | $1.06 \times 10^{-524}$ |
| rs4513773 | 6 | 44033504 | $1.58 \times 10^{-482}$ | $7.98 \times 10^{-139}$ | NA | $4.41 \times 10^{-619}$ | $1.28 \times 10^{-584}$ |
| rs9472159 | 6 | 44027673 | $2.89 \times 10^{-452}$ | $2.90 \times 10^{-109}$ | $3.58 \times 10^{-35}$ | $8.76 \times 10^{-558}$ | $7.76 \times 10^{-553}$ |

TABLE 4-continued

| SNPID | Chr | Position | p (FHS) | p (PIVUS) | p (SFS) | Meta-p (FHS + PIVUS)* | Meta-p (all)† |
|---|---|---|---|---|---|---|---|
| rs9369434 | 6 | 44026385 | $8.70 \times 10^{-443}$ | $3.02 \times 10^{-63}$ | $5.81 \times 10^{-28}$ | $1.54 \times 10^{-490}$ | $2.23 \times 10^{-496}$ |
| rs1776717 | 6 | 44059314 | $1.23 \times 10^{-19}$ | $2.27 \times 10^{-4}$ | $8.96 \times 10^{-6}$ | $2.59 \times 10^{-22}$ | $8.45 \times 10^{-27}$ |
| rs1776721 | 6 | 43998961 | $1.17 \times 10^{-19}$ | $4.34 \times 10^{-8}$ | 0.018 | $5.02 \times 10^{-26}$ | $3.12 \times 10^{-26}$ |
| rs1886979 | 6 | 44012879 | $3.23 \times 10^{-19}$ | $2.71 \times 10^{-6}$ | 0.013 | $4.82 \times 10^{-24}$ | $1.29 \times 10^{-24}$ |
| rs9472155 | 6 | 44005705 | $4.98 \times 10^{-19}$ | $4.83 \times 10^{-9}$ | 0.014 | $3.39 \times 10^{-26}$ | $1.68 \times 10^{-26}$ |
| rs844294 | 6 | 44008685 | $1.34 \times 10^{-14}$ | $1.95 \times 10^{-5}$ | 0.087 | $1.41 \times 10^{-18}$ | $2.50 \times 10^{-18}$ |
| rs4416670 | 6 | 44058431 | $2.04 \times 10^{-12}$ | 0.1 | $2.79 \times 10^{-4}$ | $1.95 \times 10^{-12}$ | $2.81 \times 10^{-15}$ |
| rs910611 | 6 | 44058829 | $4.77 \times 10^{-10}$ | $4.72 \times 10^{-6}$ | 0.11 | $1.43 \times 10^{-14}$ | $2.99 \times 10^{-14}$ |
| rs6993770 | 8 | 106650704 | $2.03 \times 10^{-16}$ | $3.61 \times 10^{-8}$ | 0.016 | $1.94 \times 10^{-22}$ | $2.96 \times 10^{-23}$ |
| rs16873402 | 8 | 106658423 | $1.45 \times 10^{-14}$ | $1.16 \times 10^{-8}$ | 0.14 | $9.09 \times 10^{-21}$ | $3.86 \times 10^{-20}$ |
| rs16873365 | 8 | 106627411 | $6.93 \times 10^{-12}$ | $2.10 \times 10^{-6}$ | 0.37 | $5.14 \times 10^{-16}$ | $2.91 \times 10^{-15}$ |
| rs7013321 | 8 | 106662734 | $4.66 \times 10^{-12}$ | NA | 0.013 | $4.66 \times 10^{-12}$ | $2.84 \times 10^{-13}$ |
| rs6993696 | 8 | 106650460 | $8.83 \times 10^{-12}$ | $1.57 \times 10^{-4}$ | 0.040 | $6.67 \times 10^{-15}$ | $1.82 \times 10^{-15}$ |
| rs16873291 | 8 | 106597206 | $5.43 \times 10^{-11}$ | $1.42 \times 10^{-6}$ | 0.061 | $1.76 \times 10^{-15}$ | $6.60 \times 10^{-16}$ |
| rs1349319 | 8 | 106625810 | $2.93 \times 10^{-8}$ | $1.73 \times 10^{-3}$ | 0.040 | $2.03 \times 10^{-10}$ | $3.05 \times 10^{-11}$ |
| rs10738760 | 9 | 2681186 | $1.17 \times 10^{-34}$ | $3.24 \times 10^{-9}$ | 0.035 | $6.36 \times 10^{-42}$ | $2.26 \times 10^{-40}$ |
| rs6475920 | 9 | 2663933 | $2.23 \times 10^{-32}$ | $1.46 \times 10^{-8}$ | 0.022 | $2.21 \times 10^{-39}$ | $3.30 \times 10^{-38}$ |
| rs4741756 | 9 | 2658187 | $2.29 \times 10^{-31}$ | $7.05 \times 10^{-6}$ | 0.097 | $2.73 \times 10^{-34}$ | $2.65 \times 10^{-32}$ |
| rs2375980 | 9 | 2682622 | $1.53 \times 10^{-27}$ | $8.92 \times 10^{-9}$ | 0.022 | $1.10 \times 10^{-34}$ | $5.61 \times 10^{-34}$ |
| rs10122587 | 9 | 2681951 | $3.89 \times 10^{-24}$ | NA | 0.026 | $3.89 \times 10^{-24}$ | $6.74 \times 10^{-24}$ |
| rs10967492 | 9 | 2671175 | $1.86 \times 10^{-21}$ | NA | 0.11 | $1.86 \times 10^{-21}$ | $2.36 \times 10^{-20}$ |
| rs10967470 | 9 | 2665698 | $2.19 \times 10^{-21}$ | NA | 0.044 | $2.19 \times 10^{-21}$ | $4.96 \times 10^{-21}$ |
| Model C | | | | | | | |
| rs6921438 | 6 | 44033585 | $3.73 \times 10^{-507}$ | NA | $3.54 \times 10^{-32}$ | $3.73 \times 10^{-507}$ | $1.22 \times 10^{-521}$ |
| rs4513773 | 6 | 44033504 | $4.54 \times 10^{-484}$ | $1.13 \times 10^{-143}$ | NA | $1.93 \times 10^{-625}$ | $3.75 \times 10^{-589}$ |
| rs9472159 | 6 | 44027673 | $5.87 \times 10^{-454}$ | $6.67 \times 10^{-113}$ | $3.49 \times 10^{-30}$ | $3.65 \times 10^{-563}$ | $7.09 \times 10^{-556}$ |
| rs9369434 | 6 | 44026385 | $4.64 \times 10^{-445}$ | $3.27 \times 10^{-65}$ | $1.76 \times 10^{-26}$ | $8.50 \times 10^{-495}$ | $1.18 \times 10^{-504}$ |
| rs1776717 | 6 | 44059314 | $8.01 \times 10^{-20}$ | $5.20 \times 10^{-4}$ | $2.77 \times 10^{-5}$ | $5.03 \times 10^{-22}$ | $4.48 \times 10^{-26}$ |
| rs1776721 | 6 | 43998961 | $1.05 \times 10^{-19}$ | $5.89 \times 10^{-9}$ | 0.025 | $8.84 \times 10^{-27}$ | $4.80 \times 10^{-27}$ |
| rs1886979 | 6 | 44012879 | $2.65 \times 10^{-19}$ | $2.12 \times 10^{-6}$ | $2.84 \times 10^{-3}$ | $3.12 \times 10^{-24}$ | $6.44 \times 10^{-26}$ |
| rs9472155 | 6 | 44005705 | $5.96 \times 10^{-19}$ | $1.33 \times 10^{-9}$ | 0.010 | $1.42 \times 10^{-26}$ | $2.46 \times 10^{-27}$ |
| rs844294 | 6 | 44008685 | $1.63 \times 10^{-14}$ | $1.95 \times 10^{-5}$ | 0.041 | $1.71 \times 10^{-18}$ | $5.41 \times 10^{-19}$ |
| rs4416670 | 6 | 44058431 | $1.16 \times 10^{-12}$ | 0.11 | $1.49 \times 10^{-4}$ | $1.38 \times 10^{-12}$ | $1.48 \times 10^{-15}$ |
| rs910611 | 6 | 44058829 | $3.37 \times 10^{-10}$ | $7.04 \times 10^{-6}$ | 0.076 | $1.39 \times 10^{-14}$ | $1.07 \times 10^{-14}$ |
| rs6993770 | 8 | 106650704 | $2.11 \times 10^{-16}$ | $6.87 \times 10^{-8}$ | $2.67 \times 10^{-3}$ | $3.12 \times 10^{-22}$ | $2.95 \times 10^{-24}$ |
| rs16873402 | 8 | 106658423 | $1.26 \times 10^{-14}$ | $1.75 \times 10^{-8}$ | 0.043 | $9.95 \times 10^{-21}$ | $2.63 \times 10^{-21}$ |
| rs16873365 | 8 | 106627411 | $7.36 \times 10^{-12}$ | $2.02 \times 10^{-6}$ | 0.26 | $5.26 \times 10^{-16}$ | $6.72 \times 10^{-16}$ |
| rs7013321 | 8 | 106662734 | $3.41 \times 10^{-12}$ | NA | $2.21 \times 10^{-3}$ | $3.41 \times 10^{-12}$ | $2.90 \times 10^{-14}$ |
| rs6993696 | 8 | 106650460 | $6.23 \times 10^{-12}$ | $2.09 \times 10^{-4}$ | $2.57 \times 10^{-3}$ | $6.00 \times 10^{-15}$ | $6.22 \times 10^{-17}$ |
| rs16873291 | 8 | 106597206 | $4.25 \times 10^{-11}$ | $9.77 \times 10^{-7}$ | 0.031 | $1.00 \times 10^{-15}$ | $1.04 \times 10^{-16}$ |
| rs1349319 | 8 | 106625810 | $2.33 \times 10^{-8}$ | $1.61 \times 10^{-3}$ | $7.71 \times 10^{-3}$ | $1.51 \times 10^{-10}$ | $1.51 \times 10^{-12}$ |
| rs10738760 | 9 | 2681186 | $1.91 \times 10^{-34}$ | $5.53 \times 10^{-8}$ | $9.24 \times 10^{-3}$ | $2.94 \times 10^{-40}$ | $7.37 \times 10^{-41}$ |
| rs6475920 | 9 | 2663933 | $3.43 \times 10^{-32}$ | $9.54 \times 10^{-8}$ | $6.55 \times 10^{-3}$ | $2.33 \times 10^{-38}$ | $8.21 \times 10^{-39}$ |
| rs4741756 | 9 | 2658187 | $5.22 \times 10^{-31}$ | $2.27 \times 10^{-4}$ | 0.049 | $2.71 \times 10^{-33}$ | $1.28 \times 10^{-32}$ |
| rs2375980 | 9 | 2682622 | $1.15 \times 10^{-27}$ | $8.63 \times 10^{-8}$ | 0.021 | $1.01 \times 10^{-33}$ | $7.71 \times 10^{-34}$ |
| rs10122587 | 9 | 2681951 | $4.10 \times 10^{-24}$ | NA | 0.027 | $4.11 \times 10^{-24}$ | $2.79 \times 10^{-24}$ |
| rs10967492 | 9 | 2671175 | $2.39 \times 10^{-21}$ | NA | 0.19 | $2.39 \times 10^{-21}$ | $3.15 \times 10^{-20}$ |
| rs10967470 | 9 | 2665698 | $2.66 \times 10^{-21}$ | NA | 0.096 | $2.66 \times 10^{-21}$ | $9.16 \times 10^{-21}$ |
| Model D | | | | | | | |
| rs6921438 | 6 | 44033585 | $1.53 \times 10^{-508}$ | NA | $1.40 \times 10^{-40}$ | $1.53 \times 10^{-508}$ | $1.51 \times 10^{-529}$ |
| rs4513773 | 6 | 44033504 | $2.35 \times 10^{-485}$ | $6.36 \times 10^{-136}$ | NA | $4.72 \times 10^{-619}$ | $1.67 \times 10^{-585}$ |
| rs9472159 | 6 | 44027673 | $1.61 \times 10^{-454}$ | $4.22 \times 10^{-108}$ | $1.52 \times 10^{-36}$ | $8.63 \times 10^{-559}$ | $3.15 \times 10^{-557}$ |
| rs9369434 | 6 | 44026385 | $6.46 \times 10^{-445}$ | $7.63 \times 10^{-63}$ | $2.70 \times 10^{-29}$ | $3.63 \times 10^{-492}$ | $3.43 \times 10^{-501}$ |
| rs1776717 | 6 | 44059314 | $2.43 \times 10^{-19}$ | $2.96 \times 10^{-4}$ | $7.08 \times 10^{-6}$ | $6.53 \times 10^{-22}$ | $1.76 \times 10^{-26}$ |
| rs1776721 | 6 | 43998961 | $7.12 \times 10^{-20}$ | $4.46 \times 10^{-8}$ | 0.013 | $3.12 \times 10^{-26}$ | $1.14 \times 10^{-26}$ |
| rs1886979 | 6 | 44012879 | $1.54 \times 10^{-19}$ | $2.15 \times 10^{-6}$ | $7.09 \times 10^{-3}$ | $1.85 \times 10^{-24}$ | $2.03 \times 10^{-25}$ |
| rs9472155 | 6 | 44005705 | $1.37 \times 10^{-19}$ | $4.11 \times 10^{-9}$ | $7.43 \times 10^{-3}$ | $7.78 \times 10^{-27}$ | $1.49 \times 10^{-27}$ |
| rs844294 | 6 | 44008685 | $2.77 \times 10^{-15}$ | $1.48 \times 10^{-5}$ | 0.048 | $2.23 \times 10^{-19}$ | $1.65 \times 10^{-19}$ |
| rs4416670 | 6 | 44058431 | $1.95 \times 10^{-12}$ | 0.088 | $2.05 \times 10^{-4}$ | $1.55 \times 10^{-12}$ | $1.74 \times 10^{-15}$ |
| rs910611 | 6 | 44058829 | $3.19 \times 10^{-10}$ | $3.45 \times 10^{-6}$ | 0.11 | $7.40 \times 10^{-15}$ | $1.70 \times 10^{-14}$ |
| rs6993770 | 8 | 106650704 | $5.19 \times 10^{-16}$ | $5.30 \times 10^{-8}$ | 0.016 | $7.22 \times 10^{-22}$ | $9.86 \times 10^{-23}$ |
| rs16873402 | 8 | 106658423 | $3.72 \times 10^{-14}$ | $1.34 \times 10^{-8}$ | 0.15 | $2.91 \times 10^{-20}$ | $1.10 \times 10^{-19}$ |
| rs16873365 | 8 | 106627411 | $2.38 \times 10^{-11}$ | $3.87 \times 10^{-6}$ | 0.36 | $2.99 \times 10^{-15}$ | $1.14 \times 10^{-14}$ |
| rs7013321 | 8 | 106662734 | $8.07 \times 10^{-12}$ | NA | 0.013 | $8.07 \times 10^{-12}$ | $4.55 \times 10^{-13}$ |
| rs6993696 | 8 | 106650460 | $1.36 \times 10^{-11}$ | $2.41 \times 10^{-4}$ | 0.040 | $1.52 \times 10^{-14}$ | $3.72 \times 10^{-15}$ |
| rs16873291 | 8 | 106597206 | $9.39 \times 10^{-11}$ | $1.37 \times 10^{-6}$ | 0.071 | $3.23 \times 10^{-15}$ | $1.30 \times 10^{-15}$ |
| rs1349319 | 8 | 106625810 | $3.87 \times 10^{-8}$ | $2.46 \times 10^{-3}$ | 0.057 | $3.66 \times 10^{-10}$ | $7.71 \times 10^{-11}$ |
| rs10738760 | 9 | 2681186 | $1.36 \times 10^{-35}$ | $1.06 \times 10^{-8}$ | 0.046 | $3.32 \times 10^{-42}$ | $1.35 \times 10^{-40}$ |
| rs6475920 | 9 | 2663933 | $9.18 \times 10^{-33}$ | $2.67 \times 10^{-8}$ | 0.018 | $1.68 \times 10^{-39}$ | $1.36 \times 10^{-38}$ |
| rs4741756 | 9 | 2658187 | $9.04 \times 10^{-32}$ | $1.28 \times 10^{-4}$ | 0.071 | $2.35 \times 10^{-34}$ | $9.51 \times 10^{-33}$ |
| rs2375980 | 9 | 2682622 | $3.07 \times 10^{-28}$ | $3.55 \times 10^{-8}$ | 0.015 | $1.02 \times 10^{-34}$ | $1.70 \times 10^{-34}$ |
| rs10122587 | 9 | 2681951 | $5.73 \times 10^{-25}$ | NA | 0.020 | $5.73 \times 10^{-25}$ | $6.91 \times 10^{-25}$ |

TABLE 4-continued

| SNPID | Chr | Position | p (FHS) | p (PIVUS) | p (SFS) | Meta-p (FHS + PIVUS)* | Meta-p (all)† |
|---|---|---|---|---|---|---|---|
| rs10967492 | 9 | 2671175 | $3.72 \times 10^{-22}$ | NA | 0.091 | $3.72 \times 10^{-22}$ | $3.50 \times 10^{-21}$ |
| rs10967470 | 9 | 2665698 | $5.48 \times 10^{-22}$ | NA | 0.045 | $5.48 \times 10^{-22}$ | $1.30 \times 10^{-21}$ |
| Model E | | | | | | | |
| rs6921438 | 6 | 44033585 | $6.58 \times 10^{-506}$ | NA | $2.91 \times 10^{-39}$ | $6.58 \times 10^{-506}$ | $7.66 \times 10^{-524}$ |
| rs4513773 | 6 | 44033504 | $6.46 \times 10^{-482}$ | $3.04 \times 10^{-138}$ | NA | $6.76 \times 10^{-618}$ | $1.66 \times 10^{-583}$ |
| rs9472159 | 6 | 44027673 | $9.84 \times 10^{-452}$ | $4.86 \times 10^{-110}$ | $4.30 \times 10^{-35}$ | $4.42 \times 10^{-558}$ | $1.30 \times 10^{-552}$ |
| rs9369434 | 6 | 44026385 | $2.44 \times 10^{-442}$ | $3.05 \times 10^{-65}$ | $5.33 \times 10^{-28}$ | $1.10 \times 10^{-492}$ | $6.10 \times 10^{-498}$ |
| rs1776717 | 6 | 44059314 | $9.92 \times 10^{-20}$ | $2.53 \times 10^{-4}$ | $1.00 \times 10^{-5}$ | $2.40 \times 10^{-22}$ | $8.47 \times 10^{-27}$ |
| rs1776721 | 6 | 43998961 | $5.41 \times 10^{-20}$ | $2.57 \times 10^{-8}$ | 0.020 | $1.47 \times 10^{-26}$ | $1.30 \times 10^{-26}$ |
| rs1886979 | 6 | 44012879 | $2.55 \times 10^{-19}$ | $1.66 \times 10^{-6}$ | 0.013 | $2.41 \times 10^{-24}$ | $7.07 \times 10^{-25}$ |
| rs9472155 | 6 | 44005705 | $1.74 \times 10^{-19}$ | $3.04 \times 10^{-9}$ | 0.015 | $7.84 \times 10^{-27}$ | $4.93 \times 10^{-27}$ |
| rs844294 | 6 | 44008685 | $8.15 \times 10^{-15}$ | $1.39 \times 10^{-5}$ | 0.086 | $6.33 \times 10^{-19}$ | $1.20 \times 10^{-18}$ |
| rs4416670 | 6 | 44058431 | $1.86 \times 10^{-12}$ | 0.11 | $2.89 \times 10^{-4}$ | $2.16 \times 10^{-12}$ | $3.14 \times 10^{-15}$ |
| rs910611 | 6 | 44058829 | $2.35 \times 10^{-10}$ | $1.99 \times 10^{-6}$ | 0.11 | $3.34 \times 10^{-15}$ | $8.62 \times 10^{-15}$ |
| rs6993770 | 8 | 106650704 | $1.34 \times 10^{-16}$ | $3.63 \times 10^{-8}$ | 0.018 | $1.27 \times 10^{-22}$ | $2.52 \times 10^{-23}$ |
| rs16873402 | 8 | 106658423 | $1.24 \times 10^{-14}$ | $8.58 \times 10^{-9}$ | 0.16 | $6.38 \times 10^{-21}$ | $3.39 \times 10^{-20}$ |
| rs16873365 | 8 | 106627411 | $8.10 \times 10^{-12}$ | $4.01 \times 10^{-6}$ | 0.37 | $9.32 \times 10^{-16}$ | $5.17 \times 10^{-15}$ |
| rs7013321 | 8 | 106662734 | $3.64 \times 10^{-12}$ | NA | 0.014 | $3.64 \times 10^{-12}$ | $2.48 \times 10^{-13}$ |
| rs6993696 | 8 | 106650460 | $5.82 \times 10^{-12}$ | $1.73 \times 10^{-4}$ | 0.047 | $4.78 \times 10^{-15}$ | $1.67 \times 10^{-15}$ |
| rs16873291 | 8 | 106597206 | $3.14 \times 10^{-11}$ | $7.92 \times 10^{-7}$ | 0.066 | $6.56 \times 10^{-16}$ | $2.99 \times 10^{-16}$ |
| rs1349319 | 8 | 106625810 | $3.53 \times 10^{-8}$ | $1.84 \times 10^{-3}$ | 0.046 | $2.60 \times 10^{-10}$ | $4.55 \times 10^{-11}$ |
| rs10738760 | 9 | 2681186 | $6.77 \times 10^{-35}$ | $3.90 \times 10^{-9}$ | 0.034 | $4.65 \times 10^{-42}$ | $1.61 \times 10^{-40}$ |
| rs6475920 | 9 | 2663933 | $1.85 \times 10^{-32}$ | $9.61 \times 10^{-9}$ | 0.022 | $1.20 \times 10^{-39}$ | $1.94 \times 10^{-38}$ |
| rs4741756 | 9 | 2658187 | $1.32 \times 10^{-31}$ | $6.02 \times 10^{-5}$ | 0.092 | $1.26 \times 10^{-34}$ | $1.22 \times 10^{-32}$ |
| rs2375980 | 9 | 2682622 | $7.94 \times 10^{-28}$ | $1.45 \times 10^{-8}$ | 0.022 | $9.69 \times 10^{-35}$ | $4.67 \times 10^{-34}$ |
| rs10122587 | 9 | 2681951 | $1.47 \times 10^{-24}$ | NA | 0.024 | $1.47 \times 10^{-24}$ | $2.56 \times 10^{-24}$ |
| rs10967492 | 9 | 2671175 | $6.75 \times 10^{-22}$ | NA | 0.10 | $6.76 \times 10^{-22}$ | $9.22 \times 10^{-21}$ |
| rs10967470 | 9 | 2665698 | $9.41 \times 10^{-22}$ | NA | 0.045 | $9.41 \times 10^{-22}$ | $2.39 \times 10^{-21}$ |

*inverse variance meta-analysis;
†effective sample size weighted meta-analysis

I claim:

1. A method for administering a VEGF-based therapy to a subject, the method comprising administering a VEGF-based therapy selected from bevacizumab, ranibizumab, lapatinib, sunitinib, sorafenib, axitinib, pazopanib, and thiazolidinedione to a subject known to have an allelic variant selected from the group consisting of:
   i. rs6921438, wherein a guanine residue is present at base 323 of SEQ ID No.1 at one or both alleles,
   ii. rs4416670, wherein a thymine residue is present at base 221 of SEQ ID Not at one or both alleles,
   iii. rs6993770, wherein a thymine residue is absent at base 235 of SEQ ID No.3 at one or both alleles, and
   iv. rs10738760, wherein a guanine residue is present at 201 of SEQ ID No.4 at one or both alleles.

2. A method for administering a VEGF-based therapy to a subject, the method comprising: screening a nucleic acid sample obtained from the subject to provide output information which identifies the presence or absence of the allelic variant rs6921438, wherein a guanine residue is detected at base 323 of SEQ ID No.1 at one or both alleles; and administering a VEGF-based therapy to the subject, wherein the VEGF-based therapy is selected from bevacizumab, ranibizumab, lapatinib, sunitinib, sorafenib, axitinib, pazopanib, and thiazolidinedione.

3. A method for administering a VEGF-based therapy to a subject, the method comprising: screening a nucleic acid sample obtained from the subject to provide output information which identifies the presence or absence of the allelic variant rs4416670, wherein a thymine residue is detected at base 221 of SEQ ID No.2 at one or both alleles; and administering a VEGF-based therapy to the subject, wherein the VEGF-based therapy is selected from bevacizumab, ranibizumab, lapatinib, sunitinib, sorafenib, axitinib, pazopanib, and thiazolidinedione.

4. A method for administering a VEGF-based therapy to a subject, the method comprising: screening a nucleic acid sample obtained from the subject to provide output information which identifies the presence or absence of the allelic variant rs6993770, wherein a thymine residue is not detected at base 235 of SEQ ID No.3 at one or both alleles; and administering a VEGF-based therapy to the subject, wherein the VEGF-based therapy is selected from bevacizumab, ranibizumab, lapatinib, sunitinib, sorafenib, axitinib, pazopanib, and thiazolidinedione.

5. A method for administering a VEGF-based therapy to a subject, the method comprising: screening a nucleic acid sample obtained from the subject to provide output information which identifies the presence or absence of the allelic variant rs10738760, wherein a guanine residue is detected at 201 of SEQ ID No.4 at one or both alleles; and administering a VEGF-based therapy to the subject, wherein the VEGF-based therapy is selected from bevacizumab, ranibizumab, lapatinib, sunitinib, sorafenib, axitinib, pazopanib, and thiazolidinedione.

6. The method of claim 2, wherein said screening comprises carrying out an in vitro assay with an array that identifies the presence or absence of the allelic variant.

7. The method of claim 3, wherein said screening comprises carrying out an in vitro assay with an array that identifies the presence or absence of the allelic variant.

8. The method of claim 4, wherein said screening comprises carrying out an in vitro assay with an array that identifies the presence or absence of the allelic variant.

9. The method of claim 5, wherein said screening comprises carrying out an in vitro assay with an array that identifies the presence or absence of the allelic variant.

10. The method of claim 2, further comprising, prior to said screening, obtaining a biological sample from the subject and isolating nucleic acid from the biological sample, to obtain the nucleic acid sample.

11. The method of claim 3, further comprising, prior to said screening, obtaining a biological sample from the subject and isolating nucleic acid from the biological sample, to obtain the nucleic acid sample.

12. The method of claim 4, further comprising, prior to said screening, obtaining a biological sample from the subject and isolating nucleic acid from the biological sample, to obtain the nucleic acid sample.

13. The method of claim 5, further comprising, prior to said screening, obtaining a biological sample from the subject and isolating nucleic acid from the biological sample, to obtain the nucleic acid sample.

14. The method of claim 10, wherein said screening comprises polymerase chain reaction (PCR), reverse transcriptase PCR (RT-PCR), isothermic amplification, nucleic acid sequence based amplification (NASBA), 5' fluorescence nuclease assay, molecular beacon assay, or rolling-circle amplification.

15. The method of claim 11, wherein said screening comprises polymerase chain reaction (PCR), reverse transcriptase PCR (RT-PCR), isothermic amplification, nucleic acid sequence based amplification (NASBA), 5' fluorescence nuclease assay, molecular beacon assay, or rolling-circle amplification.

16. The method of claim 12, wherein said screening comprises polymerase chain reaction (PCR), reverse transcriptase PCR (RT-PCR), isothermic amplification, nucleic acid sequence based amplification (NASBA), 5' fluorescence nuclease assay, molecular beacon assay, or rolling-circle amplification.

17. The method of claim 13, wherein said screening comprises polymerase chain reaction (PCR), reverse transcriptase PCR (RT-PCR), isothermic amplification, nucleic acid sequence based amplification (NASBA), 5' fluorescence nuclease assay, molecular beacon assay, or rolling-circle amplification.

18. The method of claim 14, wherein the biological sample is a blood sample.

19. The method of claim 15, wherein the biological sample is a blood sample.

20. The method of claim 16, wherein the biological sample is a blood sample.

21. The method of claim 17, wherein the biological sample is a blood sample.

* * * * *

UNITED STATES PATENT AND TRADEMARK OFFICE
CERTIFICATE OF CORRECTION

PATENT NO.        : 9,447,469 B2
APPLICATION NO.   : 14/323775
DATED             : September 20, 2016
INVENTOR(S)       : John V. Lamont Page 1 of 1

It is certified that error appears in the above-identified patent and that said Letters Patent is hereby corrected as shown below:

In the Claims

<u>Column 29,</u>
Line 23, "SEQ ID Not" should read --SEQ ID No.2--
Lines 26-27, "at 201" should read --at base 201--
Lines 62-63, "at 201" should read --at base 201--

Signed and Sealed this
Twentieth Day of December, 2016

Michelle K. Lee
*Director of the United States Patent and Trademark Office*

SEQUENCE LISTING

<160> NUMBER OF SEQ ID NOS: 9

<210> SEQ ID NO 1
<211> LENGTH: 623
<212> TYPE: DNA
<213> ORGANISM: Homo sapiens
<220> FEATURE:
<221> NAME/KEY: misc_feature
<222> LOCATION: (323)..(323)
<223> OTHER INFORMATION: "n" is A or G

<400> SEQUENCE: 1

```
attgtggtga actcaagtgt tgtagggctt aaaatgccat gcgatgttaa tcatctctgc      60
atgagcagtt catctctcca gtaaattgtg tatcacagta aagaaagatc tcttgctgtt     120
ctcacatatc tttcattgta tttagtgcaa tgctgtaaac tttgaataac accatgggat     180
ctatacgaag tgccactagt gatgctggaa gtgctcccaa gaagcagagg aaagtcatta     240
cattcaagaa aaacttgaat tgcttgatat atactgtaga ctgaggtctg cagctgtggt     300
tacccaccat ttcaagataa acnaatccac tgtaaggacc accgtgaaaa aaagaaaagg     360
aaatttgtga agccatcact gcagctatgc cagtaggcac aaaaccttgc acttttgta      420 aaatgtcttt ttatcagctt gtatggtgag tgcaggattg ctataagaaa agtataccta     480
atattcaaga agtgaagtaa ttatatgaca agttaaagca aaaggaaggt aaagactcta     540
aagctggaga atttaatgcc agcaaaggat ggtttaataa ttttaaaaag aggtttggct     600
tgaaaaatat taagataaca gaa                                             623
```

<210> SEQ ID NO 2
<211> LENGTH: 461

```
<212> TYPE: DNA
<213> ORGANISM: Homo sapiens
<220> FEATURE:
<221> NAME/KEY: misc_feature
<222> LOCATION: (221)..(221)
<223> OTHER INFORMATION: "n" is C or T

<400> SEQUENCE: 2
agctgagaag gggctggtca tggtctccct gggtgtcaaa attctagaat cagtgaatcc      60
ctgcagctca agaccttgtg cctacagtgt ctgagatgtg tgttgctcca tacgccctgg     120
ggaaccagct tctaggtaag ctctcagaaa tcccacagtg ttggagtcac aagacctctg     180
agatacagcc ctccaagttt tctatggctg caaaacaaac nattcccaaa catagtgcct     240
taaaacaata atggcttaat ttctcacaat tctggtggta gtcctggctg ttctgcaagt     300
ctaacctggg attaggccac ttaatcagct gcattcagct ggaaggtcca gggtggcctc     360
aatggcaact ctgaagcctc cgtgccatca accggcttcc gtgtgcctcc tcttagtgcc     420
tgatcctcca gagtctctct ctccagcaga atagcctgga c                        461

<210> SEQ ID NO 3
<211> LENGTH: 435
<212> TYPE: DNA
<213> ORGANISM: Homo sapiens
<220> FEATURE:
<221> NAME/KEY: misc_feature
<222> LOCATION: (235)..(235)
<223> OTHER INFORMATION: "n" is A or T

<400> SEQUENCE: 3
ctctgaagcc tcctgtctgg aatagataac cactcttgga gtatttccct ggtgctctag      60
gtttactagg ataagagcac tgatcacata actgtgagct cctgtttgct tgtctatctc     120
ccctgcagac catatgctta ttatctattt tttatctttc tatccttccc acttagaaca     180
atgtctagct tatactaaga gctcaatgaa taacattgaa tgaatcagca cattnatttt     240
ttcctttcac ttttctccat atcaggaaca gctgcacacc cctccttatt caagaccctg     300
catccttcct gaggctttac atccatgtct gtttcgtctg tgatcttgct tcatctgcct     360
aactcagcag agcaattacc acaggaaatg ctatcttgta cctgttttat ttgtttatag     420
acttgcactt ttatt                                                     435

<210> SEQ ID NO 4
<211> LENGTH: 401
<212> TYPE: DNA
<213> ORGANISM: Homo sapiens
<220> FEATURE:
<221> NAME/KEY: misc_feature
<222> LOCATION: (201)..(201)
<223> OTHER INFORMATION: "n" is A or G

<400> SEQUENCE: 4
tagccacatt ctgagggatt agggattacg acttcagcac atgaattttg aaggtacaca      60
gttcatccca tgacagggac ctgtagtagt ttctggagag ggcacaaagc agatggcagc     120
taatatccaa cgagagtcca catggaaaat gcaatttgtt tctgtgagat gcagcacctc     180
ctgatggaag gaagttggga naaatgagca ttttgaagac gcactttcca cttaccttgg     240
cacctgaaaa tcaactaggg ctcatctttt ccaaataccct ctaatcaacg gcagcaaggg    300
agaagggtga actttgggca taatgaagat gacaaaagaa ttttactgac aatgactatg     360
atgaaaactg tgaacaattt atgattttat cctcagtaca a                         401
```

<210> SEQ ID NO 5
<211> LENGTH: 501
<212> TYPE: DNA
<213> ORGANISM: Homo sapiens
<220> FEATURE:
<221> NAME/KEY: misc_feature
<222> LOCATION: (251)..(251)
<223> OTHER INFORMATION: "n" is C or T

<400> SEQUENCE: 5

```
tgaggaagga atggaaaaa aatctaatgg cagccagtaa gatgaataaa cattttccat      60
tgttttaaat atggttgtgc aagtattttt ttttactaat gcataagtgc attccttatt     120
ttctcctttc tggaactcta taatatcagg ataatgtcag tggagcagtt aatcctggtt     180
atctagaaat ggaatgggtg acccaccttt gatgttgccc tttacagcca catacctctg    240
cctggcttag ntataaagta ggaagtacca gtgtggggtt actgtgggct gaatgtctcc     300
attacctttg ggggtagaat cagctctggg agctctgttc ctgtttcctt ttggattcag     360
tatgatcttt tctgcctccc tttttcttca cctggaatga aagtggttct aggtgaaggc     420
tagtactaga ttggctaatt gcgattatca agcaaatctg catgttgaac gagactagtt     480
tttatccata tgttttattt t                                              501
```

<210> SEQ ID NO 6
<211> LENGTH: 501
<212> TYPE: DNA
<213> ORGANISM: Homo sapiens
<220> FEATURE:
<221> NAME/KEY: misc_feature
<222> LOCATION: (251)..(251)
<223> OTHER INFORMATION: "n" is C or T

<400> SEQUENCE: 6

```
taagaaggct ttttagaatg gacccaagca aaacagttgg ctattgtctg catgaaagag      60
tagggatggt ccctttttgga catgtcaccc taactaaatc tccagccata ttgtgtgcct    120
tcctataatg gtttattttg ctcaagcttc agctatcttt tattagtttc ctttatagtg     180
gtatgttatt tttatcatct ttacagtcat atgaaagggt agtggaataa tcatttccct    240
tatttcataa ntattctaac agttttcctc tgctgaatct agtagcaagt aaatgactat     300
taaaatgtat ttctttcttt aatgttttgt acatacagcc atagaagtct tgaaggaaaa    360
cttgactcag tatttattta gcatgttcca taagtcagga actcttctaa aatgtgggat     420
acaaaaatct gaatgcttcc cacacagaat tgcttcatgt aagagtatt aaatagaact      480
gaattctgtc catagccttt a                                              501
```

<210> SEQ ID NO 7
<211> LENGTH: 501
<212> TYPE: DNA
<213> ORGANISM: Homo sapiens
<220> FEATURE:
<221> NAME/KEY: misc_feature
<222> LOCATION: (251)..(251)
<223> OTHER INFORMATION: "n" is C or T

<400> SEQUENCE: 7

```
tctaccctgc attcttgtat tatttagaaa cctttgtaag aaataacaaa tcctagtatg      60
aataaaatac agatagtaat aattatggtt tacagaagta aaaatggcaa aggattatga    120
tgcccttcag ggttgcaggc tgtggttctt tgctgtctcc aggctctgcc ctactttggg     180
ctttagactt attcttagat tagttgctct catggactcc gtgcagacat tggggagtag     240
```

```
gggagctctt ntctctaggc aattttaaag aaaatatgaa cattaactct gattgctctg    300
gcttgaattg catgtccact tcttgaacca gtcattgtgc aagaaagaaa aaacaacttc    360
tttttttttt ttttttttttt tttgagatgg agttttgctc tcgttgccca ggctgcagtg   420
cagtggcgtg atcttggctc actgcaactt ctgccttccg ggtctccggg tccgagcaat    480
tctcttgcct cagcctccag a                                              501
```

<210> SEQ ID NO 8
<211> LENGTH: 916
<212> TYPE: DNA
<213> ORGANISM: Homo sapiens
<220> FEATURE:
<221> NAME/KEY: misc_feature
<222> LOCATION: (501)..(501)
<223> OTHER INFORMATION: "n" is C or G

<400> SEQUENCE: 8

```
tagtttctgt ggagactatc ttatcctcca tgaccttgct ggtgtattcc ggtgtccctc     60
ctagcagagg ggtgtggagt ttgggaccat agattttgta acatttaatt caactctgaa   120
gcatgaattc gcatttaaaa taaaagcagt ttggggctag gtgtggtggc tcatgcctgt   180
aatcccagca ctttaggagg ctgaggaggg caaatcactt gaggtcagga gtttgaggcc   240
agcctggcca acatggtgaa accccatgtc tactaaaaat acaaaaatta gctgggagtg   300
atgagtcaca cttgtaatcc cagctacttg ggaggctgag gcaggagaat cgcttgtacc   360
tgggaggcag aggttgcagt gagctgagat tgcaccactg cactgcagcc tgagtgatag   420
agtgagactc catctcaaaa ataaataaac gaaattaaat cacattaaag cagtttggac   480
tataaggtct taaaagtttt ntgcctcaaa actttggtga tgccgtcttt cccagtggcg   540
cttgtcttgt ccttttggct gacctatttt cttttctcct tttactgtgg ccactctcta   600
agattccttg tttctagggt ccttcatttc tcatagcttt ggggaattca agcccttgaa   660
gtgtcacctc aggattgggt tgccctgaat gcctcccaac ccatcctcct ctcctcagtc   720
ctttcctaaa ctcatctgcc ttgaatgcaa caaccagaat tttcttactt tcaacctttt   780
actcaatagt ttccaattat tttctccttc tcaagcttaa gccttctcaa attggatctg   840
acatccactt ttattcaaat aatgttttta tcttatgaaa aaagagatc catttagaat     900 aataattggg gcaacc                                                    916
```

<210> SEQ ID NO 9
<211> LENGTH: 601
<212> TYPE: DNA
<213> ORGANISM: Homo sapiens
<220> FEATURE:
<221> NAME/KEY: misc_feature
<222> LOCATION: (301)..(301)
<223> OTHER INFORMATION: "n" is A or G

<400> SEQUENCE: 9

```
gtatgaaaag ggacctaatt cctccccacc accctgtgca gctccgatcc cagcccttcc     60 caccccagg ccaggcctcc agggtcactg tgagcagagg gactcaggaa ggtcatggtt    120
tgggggctga gggcagagag tcccaggggc aggaatgggg acttcatcca tctctaagtt   180
tccaggtctg tgtcaggcaa tctggctctg tcctgactct ccagagactg ataaaggtcc   240
gaggtgggtg agagatgtcc acagagtctt tgctactcct actgccaaga gttggtttct   300
rttttccctc tccttgattc tggcttggcc ttatgacttg ctttgactga aaaaaatgca   360
```

```
atgatgctgt gccagtccca ggctcaaccc tagagaggcc tgactgcctt ccctccctgt    420
ctcctcttcc tccaagccag gcaccgtgct gtaaggaagt ccaggctatt ctgctggaga    480
gagagactct ggaggatcag gcactaagag gaggcgcacg gaagccggtt gatagcacgg    540
aggcttcaga gttgccattg aggccaccct ggaccttcca gctgaatgca gctgattaag    600
t                                                                   601
```